United States Patent [19]

Dürsch et al.

[11] 4,244,893

[45] Jan. 13, 1981

[54] POLYPHOSPHORUS COMPOUNDS OBTAINED BY REACTING AN ALCOHOL, PHOSPHORUS ANHYDRIDE AND AN OXALKYLATING AGENT

[75] Inventors: Walter Dürsch, Königstein; Hans-Jerg Kleiner, Kronberg; Fritz Linke, Königstein, all of Fed. Rep. of Germany

[73] Assignee: Hoechst Aktiengesellschaft, Fed. Rep. of Germany

[21] Appl. No.: 913,083

[22] Filed: Jun. 6, 1978

[30] Foreign Application Priority Data

Jun. 11, 1977 [DE] Fed. Rep. of Germany ....... 2726478

[51] Int. Cl.$^3$ ............................. C07F 9/09; C07F 9/40
[52] U.S. Cl. ................................... 260/928; 260/978; 260/980; 260/931; 260/932
[58] Field of Search ..................... 260/928, 980, 978

[56] References Cited

PUBLICATIONS

Harwood et al., "Macromolecules", vol. 1, No. 3, (1968), pp. 233–236.

*Primary Examiner*—Anton H. Sutto
*Attorney, Agent, or Firm*—Connolly and Hutz

[57] ABSTRACT

Mixtures of oligomeric phosphorus compounds which are obtained in the first step by reaction of a mono- to hexavalent alcohol with phosphinic, phosphonic and phosphoric acid derivatives containing at least one anhydride oxygen and possibly containing terminal acid P-OH radicals and by subsequent reaction in the second step with alkylene oxides or alkylene carbonates. These phosphorus compounds which contain hydroxyalkylphosphonic acid groups, may be suitably employed directly as flame-retardant finishes for textile articles or as intermediates thereof.

3 Claims, No Drawings

POLYPHOSPHORUS COMPOUNDS OBTAINED BY REACTING AN ALCOHOL, PHOSPHORUS ANHYDRIDE AND AN OXALKYLATING AGENT properties and consist of oligomeric phosphorus compounds of the general formulae $I_Z$, $I_A$, $I_K$ and $I_{bo}$

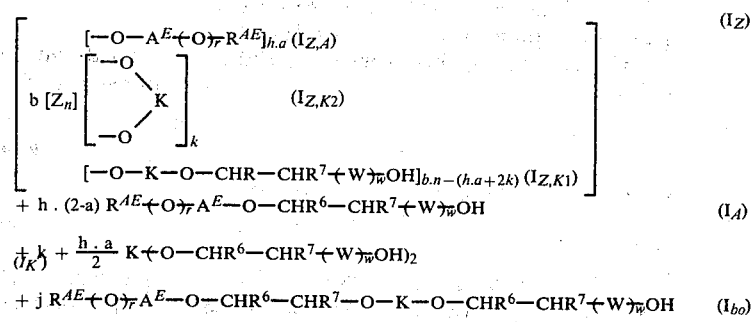

The manufacture of hydroxyalkyl polyphosphates by the reaction of polyphosphoric acid and alkylene oxides has already been described (in U.S. Pat. No. 3,099,676). The reaction products all have hydroxyl numbers which are relatively very high. As a result of this, wash-resistant fixing, for example with the aid of methylolmelamine derivatives, is made considerably more difficult. Oligomeric vinylphosphonic acid esters have been obtained by heating bis-chloroethyl vinylphosphonate, with the elimination of 1,2-dichloroethane, and these have in some cases subsequently been oxalkylated and, after free-radical crosslinking, used as flame-retardant finishes (German Offenlegungsschrift No. 2,228,698). On curing, however, difficulties can arise as a result of oxygen inhibition.

Furthermore, dialkyl phosphonates have already been converted, by the action of dihalogenoalkanes at temperatures of about 180° C., into oligomeric phosphonates, which in some cases have also subsequently been oxalkylated (U.S. Pat. No. 3,956,431). With this procedure, methyl chloride or methyl bromide usually form as undesired by-products. Both products are readily volatile toxic compounds which, for reasons of environmental protection, have to be absorbed - by a relatively involved procedure - and thus make production considerably more difficult.

Halogen-containing oligophosphoric acid esters have already been obtained using the reaction products of trishalogenophosphates and polyphosphoric acids and, optionally, in addition, phosphorus pentoxide as the starting materials, by the subsequent action of alkylene oxides - (according to German Offenlegungsschrift No. 2,036,595). However, the reaction products which have sufficiently low hydroxyl numbers are insoluble in water. They are therefore not suitable, for example, for flame-retardant finishes. Water-soluble derivatives, on the other hand, again have undesirably high hydroxyl numbers and for this reason are difficult to fix in a wash-resistant manner.

For optimum permanent flame-retardant finishes, in particular on textile floor coverings, water-soluble oligomeric phosphorus compounds with particular low or relatively high hydroxyl numbers and with specific types of phosphorus bonds and degrees of branching, which are "tailor-made" depending on the chemical nature of the substrate, are necessary.

The invention relates to mixtures (I) which have a very wide range of variation in respect of their composition and their physical, chemical and flame-retardant In these formulae:

$A^E$ denotes a group of the formulae

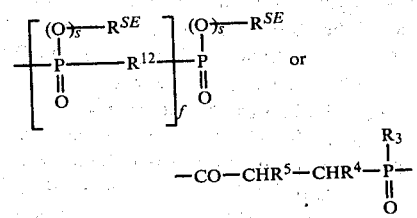

$$-CO-CHR^5-CHR^4-\overset{R_3}{\underset{\underset{O}{\|}}{P}}-$$

K denotes a group of the formulae

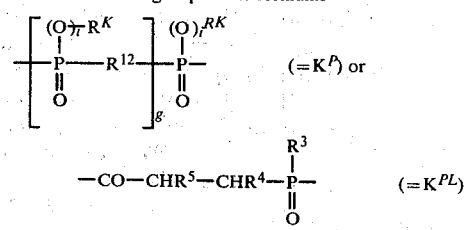

$$-CO-CHR^5-CHR^4-\overset{R^3}{\underset{\underset{O}{\|}}{P}}- \quad (=K^{PL})$$

W denotes $(-O-K-O-CHR^6-CHR^7-)_m-(-O-K-)_q$, $w=m+q=O$ to 1,200, preferably 1 to 20 and especially 1 to 5, $R^1$ denotes optionally unsaturated and/or branched alkyl radicals with 1–5 carbon atoms, which, if r is 0, can optionally be substituted by 1 or 2 chlorine or bromine atoms, preferably methyl and ethyl, $R^{SE}$ denotes the same as $R^1$ and additionally, when s is 1 and $R^{SB}$ is H, also denotes $-CHR^6-CHR^7-O-K-O-CHR^6-CHR^7+W+_wOH$, $R^{AE}$ denotes the same as $R^{AB}$ and additionally, when r is 1 and $R^{AB}$ is H, also denotes $CHR^6-CHR^7-O-K-O-CHR^6-CHR^7+W+_wOH$, $R^{SB}$ denotes the same as $R^1$ and additionally, when s is 1, denotes hydrogen, preferably methyl and ethyl and hydrogen, $R^{AB}$ denotes the same as $R^1$ and additionally, when r is 1, denotes hydrogen and, when r is 0, also denotes $CN-C_2H_4-$, preferably methyl, ethyl and hydrogen, $R^3$ denotes a $(C_1-C_4)$-alkyl group, which can optionally be substituted, preferably monosubstituted, by halogen, especially chlorine, or denotes a cycloalkyl group with up to 8 C atoms, especially cyclopentyl or cyclohexyl, an alkylene group with up to 4 C atoms, especially vinyl and allyl, or a phenyl or benzyl group, which can optionally be substituted, preferably monosubstituted to trisubstituted, by halogen, preferably chlorine and/or bromine, $R^4$ denotes hydrogen or a $(C_1-C_4)$-alkyl group, preferably methyl, and $R^5$ denotes hydrogen or a ($C_1$–$C_2$)-alkyl group, preferably methyl, and preferably at least one of the radicals $R^4$ and $R^5$ is hydrogen, $R^6$ denotes hydrogen, methyl or chloromethyl, $R^7$ denotes hydrogen, methyl or ethyl, preferably hydrogen, $R^{12}$ denotes alkylene, cycloalkylene, arylene or aralkylene, preferably ($C_1$–$C_6$)-alkylene, phenylene or p-xylylene, or phosphorus-containing radicals of the formula

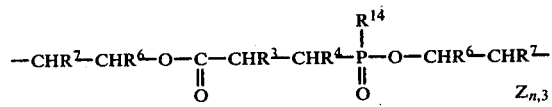

in which $R^4$, $R^5$, $R^6$ and $R^7$ are as defined above and $R^{14}$ has the meanings defined for $R^3$ or denotes the group —O—$CHR^6$—$CHR^7$—, m denotes 0 to 1,200, preferably 1 to 20 and especially 1 to 6, preferably 2 to 4, q denotes 0 or 1, preferably 0, b denotes 2/6 to 1,200, preferably 1 to 20 and, when $R^{AB}$ and/or $R^{SB}$ are hydrogen, optionally also denotes 0, f, g and h denote 0 or 1, r and s denote 0 or 1, a denotes 0, 1 or 2, j denotes 0 or 1, but denotes 0 only when b=0 and $R^{AB}$ and/or $R^{SB}$ are hydrogen, k denotes 0 to n-h·a/2, preferably 0, $C^K$ denotes the number of core anhydride equivalents and is from 2 to 1,200, preferably from 3 to 30, and $Z_n$ denotes a functional radical from the group of straight-chain or branched hydrocarbon radicals with 1 to 18, preferably 1–12, C atoms, which can optionally be interrupted by up to eight —O— and in general by up to (y/2-1) —O—, when y is the number of C atoms in $Z_n$, or by up to two carboxylate groups (—O—CO—) and by up to three —S— and/or $NR^2$ radicals in which $R^2$=($C_1$–$C_4$)-alkyl, especially methyl, and/or can optionally be substituted, preferably to replace up to half of the H atoms contained in $Z_n$ and especially monosubstituted to tetrasubstituted, by fluorine, chlorine or bromine atoms, preferably Cl or Br, or aromatic or araliphatic radicals which are derived from benzene or alkylenebenzenes with up to 18 C atoms or from naphthalene, diphenyl, diphenylmethane, diphenylethane or 2,2-diphenylpropane and which can optionally be substituted in the nucleus by 1 or 2 methoxy or ethoxy groups and can be substituted, preferably up to pentasubstituted, in the nucleus and/or the side chains by F, Cl or Br atoms, or phosphorus-containing radicals of the general formula

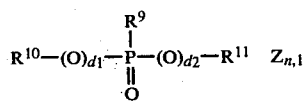

in which $d_1$ and $d_2$ independently of one another are 0 and 1 and $R^9$ is alkyl, hydroxyalkyl, optionally ($C_1$–$C_2$)-alkylated or -dialkylated aminoalkyl, halogeno (preferably Cl)-alkyl with 1 to 3 C atoms, alkenyl with 2 or 3 C atoms or phenyl, which can optionally be substituted by 1 or 2 halogen atoms, preferably Cl or Br, and $R^{10}$ and $R^{11}$ have the same meaning as $R^9$ when $d_1$ or $d_2$ is 0, or $R^{10}$ and $R^{11}$ denote a ($C_1$–$C_3$)-alkylene radical when $d_1$ and $d_2$ are simultaneously 0, and denote a straight-chain or branched alkylene radical with 2–5 C atoms or the radical

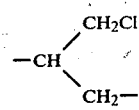

when $d_1$ and $d_2$ are 1, or phosphorus-containing radicals of the general formula

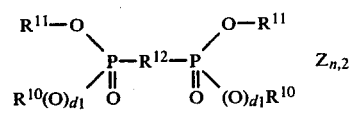

in which $d_1$, $R^{10}$ and $R^{11}$ are as defined in $Z_{n,1}$ and $R^{12}$ is as defined above.

The letters B, E, A, S and K used as superscripts in the above formulae to provide a better overall picture have the following meaning: B signifies "start" with respect to time, E is "end" with respect to time, A is "outer radical", S is "side radical" and K is "core radical".

The reaction mixtures (I) are obtained by, if b>0, mixing b moles of a n-hydric alcohol of the formula $$Z_n(-O-H)_n \qquad (II)$$

by a multi-stage process (MSP) with about b·n+e anhydride equivalents of organic phosphorus anhydrides (III) of the general formula

where e is the number of free acid radicals in the organic phosphorus anhydrides (III) and represents numbers from 0 to 6, preferably 2–4, when b is 0 or 1, and 0 when b is 2 to 6, $A^B$ denotes a group of the formulae

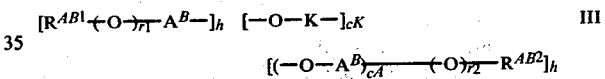

or

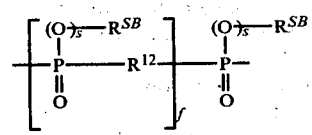

$R^{AB1}$ denotes the same as $R^{SB}$ and $R^{AB2}$ denotes the same as $R^{SB}$ and, when $r_1$=0, also denotes $CN$—$C_2H_4$—, K denotes 1 to $c^K$ times a group of the formula

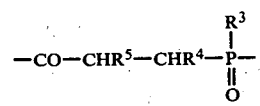

or 0 to $c^K$-1 times a group of the formula

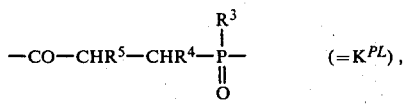  $(=K^{PL})$, h denotes the same as above, $R^K$ denotes the same as $R^1$ and additionally, when i is 0, also CN—C$_2$H$_4$—, r$_1$ and r$_2$ denote the same as r, b denotes the same as above, f denotes the same as above, $c^A$ denotes 0 or 1, $c^K$ denotes the same as above and c denotes the total number of all possible anhydride equivalents in III, and in accordance with $c = c^A + c^K = (m+l+q)\cdot(b\cdot n+e)$ denotes 2 to 1,201, reacting the mixture at temperatures of 0° C. to 180° C., preferably 80° C. to 150° C., to give an acid mixture (SR) of phosphorus-containing acids or esters of the general possible composition

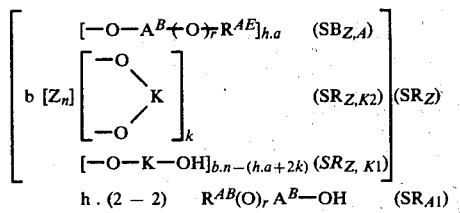

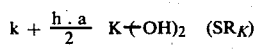

and

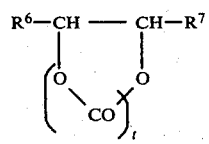

and, after the reaction has ended, which is discernible by the disappearance of the anhydride bands, mixing the resulting acid reaction product (SR), in which q=1, with the b.n+e-fold molar amount of an oxalkylating agent of the formula

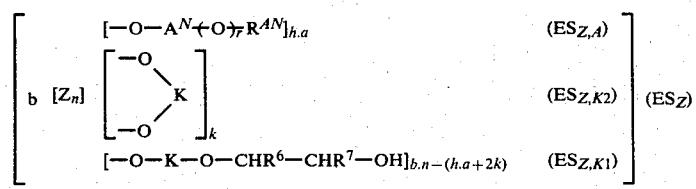  (IV)

in which t denotes 0 (alkylene oxides (IV$_o$)) or 1 (alkylene carbonates (IV$_1$)), converting the mixture, at temperatures of 20° C. to 240° C., preferably 60°–180° C., when t=0 and at temperatures of 80° to 240° C., preferably 150° to 220° C. when t=1, to the corresponding neutral hydroxyalkyl ester mixture (ES), in which m is 0 and q is 0, consisting in total of the following esters

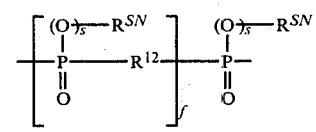

or

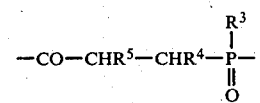

and $R^{SN}$ denotes the same as $R^1$ and additionally, when s=1 and $R^{SB}$ was hydrogen, also —CHR$^6$—CHR$^7$—OH, $R^{AN}$ denotes the same as $R^{SN}$ and additionally, when r=0, also CN—C$_2$H$_4$—, and N as a superscript denotes "neutralized", and, after the reaction has ended, which is discernible by the disappearance of the acid number and, when t=1, also of the evolution of CO$_2$, repeating, at the above reaction temperatures, the addition of b.n+e anhydride equivalents (m+q) times and then the oxalkylation of the particular acid intermediate products—a total of m times.

Another process, the so-called direct process (DP) comprises mixing an alcohol of the formula II with a total of $c = (b\cdot n+e)(m+l+q)$ anhydride equivalents of organic phosphorus anhydrides of the formula III and optionally an oxalkylating agent (IV) of low volatility, at temperatures of 80° C. to 180° C., preferably 100° to 150° C., and, after the heat of reaction has subsided, reacting the mixture with the approximately $u = (b\cdot n + e)\cdot(m+l)$-fold molar amount of an oxalkylating agent of the formula IV, where u denotes the total number of moles thereof, preferably with stirring, at the particular oxalkylation temperatures, until the reaction has ended - which is discernible by the disappearance of the anhydride bands and, when t=1, also of the evolution of CO$_2$ and, when q=0, also of the acid number.

When b is 0, j is 1 and e is at least 1 and preferably 2–4, it is also possible very simply, by a single-stage process (SSP), to react $c = e\cdot(m+1+q)$ anhydride equivalents of the phosphorus anhydrides of the formula III containing e acid end or side groups, at the particular oxalkylation temperatures, with only about c moles of the oxalkylating agents (IV) until end reaction compounds, which are still acid, of type I$_{bo}$ (in which q=1) have formed or with at least about e+c moles of IV until neutral 2-hydroxyalkyl esters of type I (in which q=0) have formed.

The undesired alcohol-free cyclic reaction products

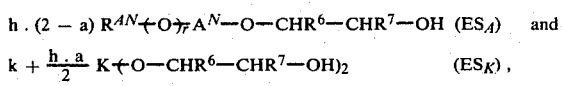

in which $A^N$ denotes of the formula

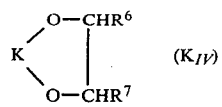

which may have formed in the direct or single-stage processes described above and consist only of core anhydrides (K) and the oxalkylating agents (IV) can to an extremely large extent be destroyed and converted to substances of the type $I_Z$, $I_A$, $I_K$ and/or $I_{bo}$ by subsequently heating to 100° to 200° C., preferably 130° to 170° C. - optionally, for example, in the presence of alkaline catalysts, preferably sodium carbonate - and/or by after-treatment with alkaline catalysts, such as, for example, preferably sodium methylate, at temperatures of 0° to 100° C., preferably 20° to 60° C.

The moles of the compounds $I_Z$ are generally formulated for monohydric to hexahydric alcohols. For example, in the special case, which is not preferred, of only monohydric alcohols ($Z_1$-OH), in which $Z_1$ denotes an alcohol radical which is only monovalent and n is 1, a total of b moles of the end reaction mixtures $I_Z$ containing the phosphorus ester groups form, since b equivalents of $Z_1$ are present. When the anhydride groups are reacted with alcohols (II), there are now, however, many arbitrary possibilities for the primary attack. Therefore, when n is 1, compounds of very diverse types can be present amongst the total b moles in the mixture $I_Z$. When h=1 and a is 1 or 2, that is to say when the starting materials III are, for example, terminated organic phosphorus anhydrides, the b moles of the mixture $I_Z$ can include, as desired, 0 to 2 (or h·a₁) moles of full esters of the hydroxyl group-free type

in rare cases (if full esterifications have taken place on the same P atom) also a few (k) moles of the type

which is also free from hydroxyl groups, and, accordingly, b−(h·a+2k) moles of the oligomeric main products

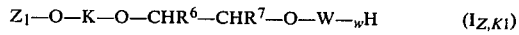

which contain hydroxyl groups and are by far the predominant products.

The 0 to 2 (or h·(2-a)) moles of the end reaction compounds $I_{A1}$ and the (k+h·a/2) moles, which is also a low number, of the end reaction compounds $I_K$ never contain any alcohol radicals ($Z_n$). They are therefore always able to form, circumstances permitting—independently of the functionality (n) of the alcohols (II). This, of course, also applies correspondingly to all acid intermediate compound mixtures, starting at SR and up to the penultimate mixture, which appropriately can be characterized by $I_{m-1,q1}$, but also to all neutral intermediate compound mixtures, from ES to the penultimate mixture having the characteristic $I_{m-1,q0}$.

When b>0, the process according to the invention is in general carried out by initially introducing the phosphorus anhydrides of the formula III and, additionally, where appropriate, alkylene oxides (IV) or alkylene carbonates (IV₁) of low volatility, if such are used, at room temperature and slowly adding the alcohol (II) at a temperature above the temperature required to effect dissolution. However, the alcohols (II) can usually also additionally be initially introduced.

The heats of reaction which arise when the compounds II and III react with one another remain below the hazard level - especially when alkylene carbonates (IV₁) are present.

The rates of reaction are distinctly increased and side reactions are suppressed by the addition of basic catalysts in amounts of 0.05-4.0%, preferably 0.2-2.0%, based on the sum of the compounds II, III and IV employed, the catalysts preferably being chosen from the group comprising the alkali metal hydroxides, such as NaOH or KOH, the alkali metal ($C_1$-$C_4$)-alcoholates, such as Na methylate or K tert.-butylate, the alkali metal (bi)-carbonates, such as sodium carbonate, potassium carbonate, Na bicarbonate or K bicarbonate, and the tertiary amines, such as triethylamine and triethanolamine. The reaction times are in general between about 1 and 120 hours, preferably 1 and 20 hours, depending on the reaction temperature. They are, of course, longer as m increases, especially for m>3, than for a low m.

It is, of course, possible also to produce alcohols of the formula II just shortly before the addition of the phosphorus anhydrides (III), by reacting alkylene oxides (IV₀) and/or alkylene carbonates (IV₁) with free carboxylic, phosphinic or phosphonic acids, and then to react these further in accordance with the invention. In this case, the v-molar amount of alkylene oxides or alkylene carbonates, when v is the number of free acid groups, would additionally be required beforehand.

The stepwise formation of the compounds according to the invention (of type $I_Z$) with recurring atom groupings can, for example, in a simple case, when h and a are 0 and b is 1, be formulated in the following way, using a dihydric alcohol, such as, for example, glycol, as compound II, 1,2-ethane-bis-(methylphosphinic acid) anhydride, as compound III, and ethylene oxide, as compound IV, as the starting materials:

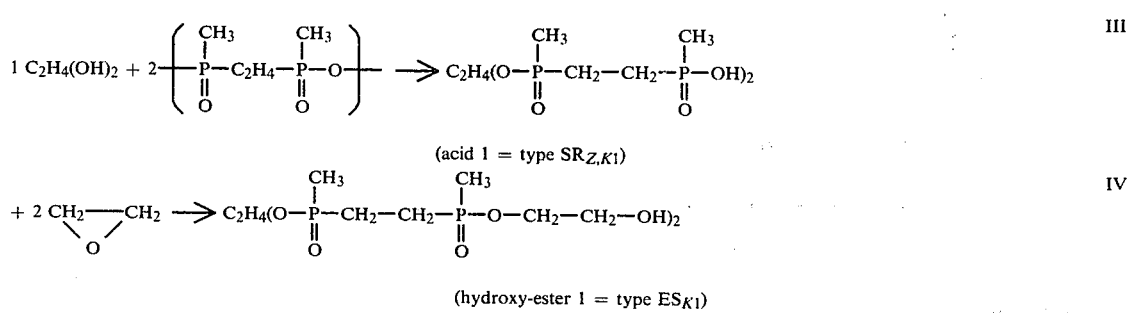

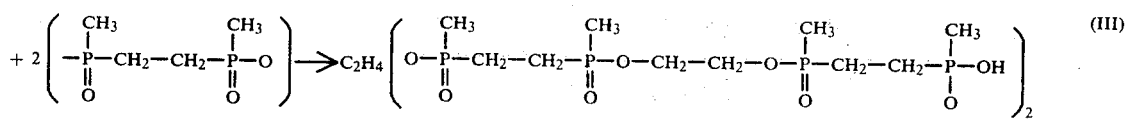

(acid 2 = type $I_{Z,K1,m0,q1}$)

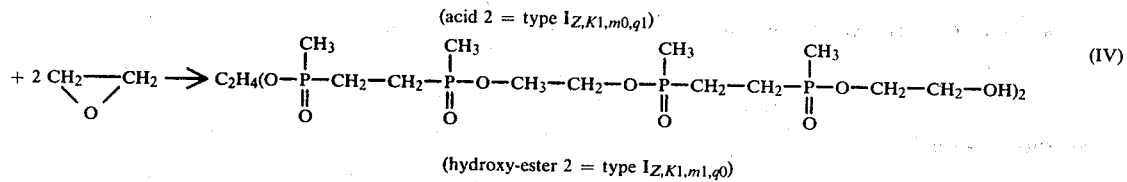

(hydroxy-ester 2 = type $I_{Z,K1,m1,q0}$)

The chain can lengthen even further with further molecules of III and IV. If $l+m$ is the number of molecules of IV used in total per lengthening chain, acids 1, 2, 3, 4 and the like (in general $1+m+q$) always form when q moles of III, or one mole more of III than of IV (in general $1+m+q$ moles of III) are used for the reaction.

Neutral 2-hydroxyalkyl esters 1, 2, 3, 4 and the like result when the number of molecules of IV reacted at least corresponds to the number of molecules of III, that is to say is likewise at least $1+m$ (in this case $q=0$). Analogous formulations result when the starting material is not a dihydric alcohol, such as, for example, glycol ($n=2$), but n-hydric alcohols with the general formula Z $(—OH)_n$, in which $Z_n$ has the general meaning indicated.

Mixtures of alcohols of the formula II can be used as the starting materials and in this case correspondingly more complex mixtures of compounds of the formula I are obtained. However, it is also possible to use mixtures of compounds of the formula III and/or IV as the starting materials, and corresponding mixtures of the formula I are obtained. It is also possible simultaneously to use both the compounds $IV_1$, that is to say alkylene carbonates, and also the compounds $IV_0$, that is to say alkylene oxides, for the oxalkylation reactions. In this way, the favorable solution properties of the alkylene carbonates can be combined with the usually somewhat more advantageous price of the alkylene oxides.

When $e>0$ and b is 0, that is to say no alcohols (II) are employed, the end products which result are predominantly only the compounds $I_{bo}$. The stepwise formation of these products can be illustrated by an idealized reaction equation, for example using ethylene oxide (IV) and a specific organic phosphorus anhydride ($III_{SP}$), in which $e=2$, which comprises 4 anhydride equivalents of ethane-phosphonic acid anhydride and 1 mole of methane-phosphonic acid and is of the formula

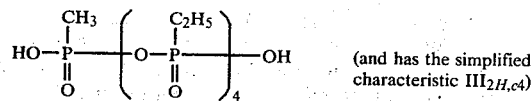

(and has the simplified characteristic $III_{2H,c4}$)

as the starting materials, any side reactions being disregarded. The intermediate compounds can again be characterized by the symbols SR and ES and the end products can be characterized by I with index notations. In this case, the substance III can be characterized, after the first oxalkylation, as a dineutralized type ($III_{2N,c4}$).

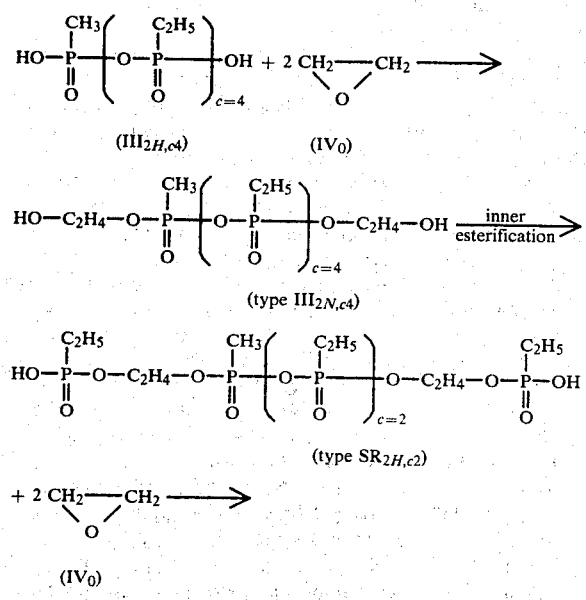

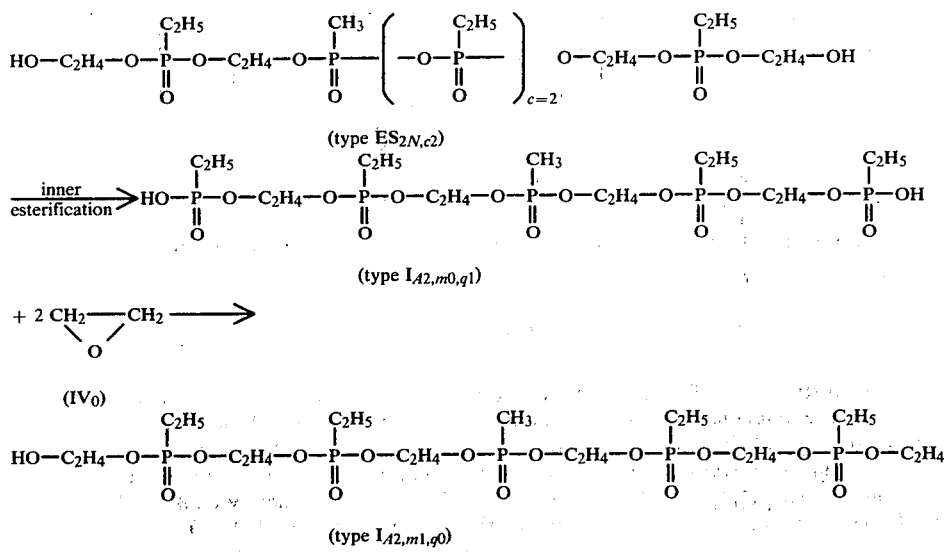

If, for example, in another compound III$_{SP}$ only one acid hydroxyl end group is present (R$^{AB2}$=—OH), that is to say e is 1 and R$^{AB1}$ is, for example, C$_3$H$_7$ and r$_1$ is 0, the compound is a reaction product of methylpropylphosphinic acid and ethanephosphonic acid anhydride. On reaction with, for example, 5 moles of ethylene oxide (IV$_0$), the chain then lengthens on one side only. In the end product (I$_{m3,q0}$) m is then 3 and q is then 0.

The manufacture of reaction products I$_{bo}$, which are still acid, always requires u$_{SR}$=c moles of ethylene oxide (IV$_o$) and that of neutral end products I$_{bo}$ always requires in general at least u$_N$=e+c moles of ethylene oxide (IV$_o$).

Amongst the monohydric organic hydroxy compounds (Z$_1$—OH) for which n=1, which can be employed when b>0, examples of compounds which can be used are all the readily accessible aliphatic straight-chain and branched alcohols having 1 to about 18 C atoms. Examples of the most important compounds which may be mentioned are: methanol, ethanol, n-propanol, i-propanol, n-butanol, sec.-butanol, n-hexanol, 2-ethyl-1-butanol, n-octanol, 2-ethyl-1-hexanol, n-dodecanol, n-hexadecanol and n-octadecanol, the alcohols having 1 to 4 C atoms being preferred. Polyhydric alcohols, for which n=2-6, are even more suitable than monofunctional alcohols, when e is 0.

Examples which may be mentioned of the polyhydric aliphatic polyols for which n=2-6 are: ethylene glycol, 1,2-propylene glycol, 1,3-propylene glycol, 1,4-butanediol, neopentylglycol, 1,6-hexanediol, glycerol, trishydroxymethylethane, trishydroxymethylpropane, pentaerythritol, sorbitol and mannitol. Glycerol, pentaerythritol and 1,6-hexanediol are particularly suitable.

Examples of unsaturated alcohols which may be mentioned are: n-but-2-en-1-ol, 1,4-butenediol and allyl alcohol, 1,4-butenediol being preferred as a dihydric alcohol.

Amongst the numerous compounds in which one or more —CH$_2$ groups in an aliphatic hydrocarbon radical have been replaced by ether bridges —O—, suitable compounds are, for example, the reaction products of monohydric alcohols with one or more molecules of alkylene oxides or alkylene carbonates, such as, for example, 2-methoxy-ethanol, 2-ethoxy-ethanol, 2-butoxy-ethanol, 2-(2'-ethyl-hexyloxy)-ethanol and 2-n-dodecyloxy-ethanol, and also the reaction products of 1 mole of methanol, 1 mole of ethanol or 1 mole of isopropanol and 2 moles of ethylene oxide or an alkylene carbonate, that is to say so-called methyldiglycol, ethyldiglycol and isopropyldiglycol, and also the reaction products of 3 to 7 molecules of ethylene oxide or ethylene carbonate with 1 mole of methanol, ethanol or isobutanol.

Suitable reaction products of ethylene oxide and dihydric alcohols are, for example, so-called diglycol, so-called triglycol and the higher reaction products of ethylene oxide and/or ethylene carbonate with water or ethylene glycol which have up to 18 C atoms, the so-called polyethylene glycols of various molecule sizes up to an average molecular weight of 400, especially diglycol and triglycol; further suitable compounds are, for example, the adducts of 1-6 molecules of ethylene oxide and/or ethylene carbonate with trihydric or higher-hydric alcohols (n=3-6), such as, for example, glycerol, trishydroxymethylpropane, pentaerythritol and the like.

In addition to reaction products of ethylene oxide and/or ethylene carbonate and monohydric or polyhydric alcohols, reaction products of monohydric and polyhydric alcohols with other 1,2-alkylene oxides and-/or 1,2-alkylene carbonates, such as, above all, 1,2-propylene oxide, 1,2-propylene carbonate or epichlorohydrin, can also be used, as can the reaction products of ethylene oxide and/or ethylene carbonate with poly-1,2-propylene glycols, which latter reaction products are—as is known—manufactured in a wide variety as surface-active compounds. Corresponding poly-1,2-propylene glycols and corresponding adducts of ethylene oxide and/or ethylene carbonate and (poly)-1,2-propylene oxides may be mentioned in particular.

In addition to —O— bridges, the hydrocarbon chain of aliphatic hydroxy compounds can also be interrupted by other hetero-atoms, such as, for example, by the elements N, S and/or P or by carboxylic acid ester groups. These compounds can, for example, be obtained particularly simply by reacting one or more molecules of 1,2-alkylene oxides and/or 1,2-alkylene carbonates with ammonia, primary or secondary amines, hydrogen sulfide or mercaptans and with oxy-acids of phosphorus, ($C_2$–$C_6$)-carboxylic acids or dicarboxylic acids.

Examples which may be mentioned of the reaction products of these compounds with 1,2-alkylene oxides or 1,2-alkylene carbonates are:

Those containing N in the molecule: the tertiary alkanolamines, such as, for example, triethanolamine, methyldiethanolamine, n-butyl-diethanolamine, tetrahydroxyethyl-ethylenediamine, pentahydroxyethyl-diethylenetriamine, n-dodecyl-diethanolamine, dimethylethanolamine, n-butyl-methylethanolamine, di-n-butyl-ethanolamine and n-dodecylmethylethanolamine and correspondingly higher reaction products of these tertiary amines with ethylene oxide or ethylene carbonate or propylene oxide or propylene carbonate up to a total C number of 18 C atoms in the molecule.

Those containing S in the molecule: bis-(2-hydroxyethyl) sulfide, bis-(2-hydroxypropyl) sulfide and bis-(2-hydroxyethyl)-sulfone and their reaction products with further ethylene oxide or ethylene carbonate or propylene oxide or propylene carbonate up to a total C number of 18 C atoms in the molecule.

Those containing P in the molecule: neutral reaction products of 1,2-alkylene oxides, such as ethylene oxide, propylene oxide and epichlorohydrin, in particular ethylene oxide, or, for example, ethylene carbonate, with monobasic and polybasic alkanephosphonic acids with 1 to 18 C atoms, such as, for example, with n-butane-, isobutane-, 2-ethyl-hexane, n-octane-, decane-, dodecane- and tetradecane-phosphonic acid, but especially with methane-, ethane-, propane- and vinyl-phosphonic acid and 1,2-ethane- or 1,4-butane-diphosphonic acid, and also with monobasic or polybasic dialkyl-phosphinic acids, such as, for example, methyl-butyl-phosphinic acid, methyl-n-octyl-phosphinic acid, methyl-n-dodecyl-phosphinic acid and especially dimethyl-, ethyl-methyl- and methyl-propyl-phosphinic acid and 1,10-decane-bis-(methyl-phosphinic acid), methyl-vinyl-phosphinic acid and ethane-1,2-bis(methyl-phosphinic acid).

Furthermore, reaction products of 1 to 7 moles of alkylene oxide or ethylene carbonate with monobasic aliphatic carboxylic acids such as, for example, above all acetic acid, propionic acid and butyric acid, and polybasic aliphatic carboxylic acids, such as, for example, succinic acid and adipic acid, but also unsaturated carboxylic acids, such as crotonic acid and, preferably, (meth-)acrylic acid are also suitable.

In addition to hydroxy compounds of this type which contain hetero-atoms N, S and P and are very readily accessible by oxalkylation reactions, numerous further compounds containing hydroxyl groups and optionally these hetero-atoms and/or carboxylic acid ester groups in the hydrocarbon chain are also suitable; amongst these compounds only oligo-condensation products, which form by the reaction of dicarboxylic acids or dicarboxylic acid anhydrides with polyhydric alcohols, and also methyl glycollate, ethyl 2-hydroxyethane-carboxylate and the like are mentioned as examples.

Further suitable compounds are, for example, dimethyl hydroxymethane-phosphonate, diethyl 2-hydroxyethane-phosphonate, di-n-butyl 3-hydroxypropane-phosphonate and the like and analogous compounds from the phosphinic acid series, such as, for example, methyl hydroxymethyl-methyl-phosphinate, ethyl 2-hydroxyethyl-methyl-phosphinate, 2'-ethylhexyl 3-hydroxypropyl-methyl-phosphinate, hydroxymethyl-dimethyl-phosphine oxide and 2-hydroxyethyl-dimethyl-phosphine oxide.

All of the aliphatic hydroxy compounds which have been mentioned, and analogous aliphatic hydroxy compounds which have not been named, can be substituted by the halogen atoms chlorine, bromine and fluorine, especially by chlorine and bromine. Examples which may be mentioned are the following readily accessible compounds, which are of interest because of their advantageous flameproofing properties: 2-bromoethanol, 2,3-dibromo-1-propanol, 2,3-dibromo-butane-1,4-diol, bis-(2-hydroxyethyl) dibromosuccinate, bis-(2-hydroxyethyl) 2,3-dibromopropane-phosphonate, bis-(2,3-dibromopropyl) 2-hydroxyethanephosphonate and also chloroethanol, 2,3-dichloro-1-propanol, 1,3-dichloro-2-propanol, 2,3-dichloro-butane-1,3-diol, bis-(2,3-dichloropropyl) 2-hydroxyethanephosphonate, bis-(2-hydroxyethyl) 1-chlorovinylphosphonate and the like.

The selection of suitable aromatic compounds which carry n OH radicals is also very wide.

Amongst the aromatic compounds, those which are preferred are all aromatic compounds which contain alcoholic hydroxyl groups, such as, for example, benzyl alcohol and all 2-hydroxyalkyl ethers or esters, which are formed by oxalkylation of phenolic hydroxyl groups or of aromatic compounds, which contain carboxylic acid radicals, phosphonic acid radicals or phosphinic acid radicals, with compounds of the formula $IV_o$ and $IV_1$.

Aromatic compounds which can be used for the reaction with 1,2-alkylene oxides ($IV_o$) or 1,2-alkylene carbonates ($IV_1$), in order to manufacture aromatic starting materials II containing alcoholic hydroxyl groups, are therefore, in addition to mononuclear and binuclear aromatic compounds containing phenolic hydroxyl groups, above all, for example, aromatic mono- and di-carboxylic acids, such as, for example, benzoic acid, phthalic acid, isophthalic acid, terephthalic acid, 1-naphthalenecarboxylic acid, 2-naphthalenecarboxylic acid and the diverse naphthalenecarboxylic acids, but also aromatic hydroxycarboxylic acids, such as, for example, the three different hydroxy-benzoic acids, the various naphthol-carboxylic acids, 4,4'-diphenyl-dicarboxylic acid and the like.

In special cases, aromatic chloro- and especially bromohydroxy compounds, such as, for example, the oxalkylation products of 2,4,6-tribromo-phenol, pentabromo-phenol, 2,4,6-trichloro-phenol or pentachlorophenol and 2,2-bis-(4-hydroxy-3,5-dibromo-phenyl)-propane, can be of particular interest because of their advantageous influence on the flameproofing properties.

Likewise, for example, all other aromatic carboxylic acids which contain bromine, chlorine or fluorine and are derived from benzene and naphthalene, such as, above all, for example, tetrabromo- and tetrachlorophthalic acid, are suitable. The reactions with the compounds IV can in this case also again take place directly prior to the action of the compounds III, so that a special oxalkylation process can optionally be dispensed with, especially when developing industrial processes.

Likewise, aromatic phosphonic or phosphinic acids, such as, for example, benzenephosphonic acid, 1,3- and 1,4-phenylene-diphosphonic acid, phenyl-methyl-phosphinic acid, 1,3- and 1,4-phenylene-bis-(methylphosphinic acid) and the like can be converted beforehand into the corresponding 2-hydroxyalkyl esters by reaction with the 1,2-alkylene oxides (IV$_o$) and/or 1,2-alkylene carbonates (IV$_1$).

Suitable aromatic compounds containing alcoholic hydroxyl groups can, however, also be obtained by prior reactions of aromatic amines or mercapto compounds with 1,2-alkylene oxides and/or 1,2-alkylene carbonates.

Examples which may be mentioned of aromatic compounds which contain amino groups and are suitable for oxalkylation reactions are: aniline, methylaniline, o-, m- and p-phenylene-diamine, the diverse o-, m- and p-toluidines and -anisidines, -aminophenols, -amino-benzoic acids and -aminobenzene- sulfonic acids, 1- and 2-naphthylamines, the diverse amino-naphthols and also 4,4'-diaminodiphenylmethane, 4,4'-benzidine, the possible chloro- and bromo-anilines and, above all, 2,4,6-tribromoaniline and the like, but also phenylalkylamines, such as, above all, benzylamine or methyl-benzylamine and dibenzylamine.

Examples which may be mentioned of aromatic mercapto compounds which can be oxalkylated are: phenylmercaptan, p-toluyl-mercaptan, - or 2-naphthylmercaptan and the like.

The suitable organic phosphorus anhydrides of the general formula III

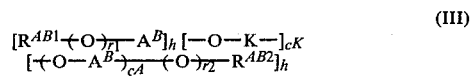 (III)

can be very diverse depending on which specific meanings $R^{AB1}$, $R^{AB2}$, $r_1$, $r_2$, $A^B$, K, h, $c^K$, $c^A$ and also $R^{SB}$, $R^K$, $R^{12}$, f, g, s and i possess.

The compounds III can be subdivided in accordance with their spatial structure into III$_{AG}$ "terminated organic phosphorus anhydrides", in which h is 1 and, thus, two mono-outer groups ($R^{AB}$—$A^B$—) are also always present, and into III$_{EC}$ "true organic phosphorus anhydrides" (h=0), and the latter can be further subdivided into III$_{OF}$ "open-chain organic phosphorus anhydrides", which are linear and polymeric and in which h=0 and $c^K$ is infinite in the ideal case, and into III$_{CY}$ "cyclic organic phosphorus anhydrides", in which, although h is likewise 0, the anhydrides are closed within themselves, that is to say are cyclic compounds. Rings containing, for example, 4, 5, 6 or 8 ring members can exist. They can contain, per ring, optionally $c^{K,CY}$=1, 2, 3, 4 or even more anhydride equivalents. The "true open-chain" anhydrides and the "true cyclic" anhydrides are frequently in equilibrium. Therefore, it is entirely possible for linear open-chain organic phosphorus anhydrides III$_{OF}$ to exist alongside cyclic III$_{CY}$. It is completely immaterial for the course of reaction whether or not proton-free cyclic anhydrides (III$_{CY}$) may also be present alongside open-chain anhydrides (III$_{OF}$) when proton-free phosphorus anhydrides (III$_{EC}$) are reacted. Ultimately, it is only the effective total content of anhydride equivalents (c), which is expressed by the symbol $c=c^K+c^A$, which is decisive.

The value $c^K$ can also include $c^{K,CY}$ cyclic phosphorus anhydrides of type III$_{CY}$ in addition to $c^{K,OF}$ open-chain phosphorus anhydrides of type III$_{OF}$, in accordance with $c^K=c^{K,CY}+c^{K,OF}$.

In accordance with the above definition, K can be

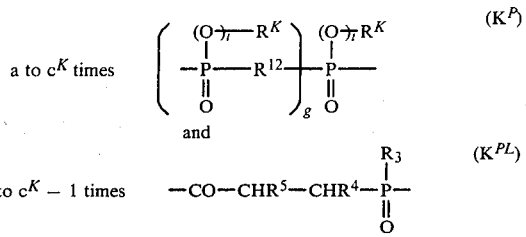

The compounds III$_{CY}$, which may additionally be suitable, therefore include, for example, the clearly cyclic phosphine-carboxylic acid anhydrides of the "phospholane type" (III$_{PL}$)

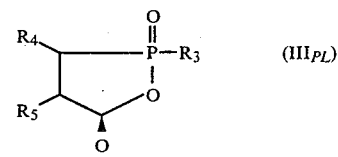 (III$_{PL}$)

such as, for example, 2-methyl-, 2-ethyl-, 2-n-propyl-, 2-isobutyl-, 2-vinyl-, 2-chloromethyl-, 2-phenyl-, 2,3-dimethyl-, 2-methyl-3-ethyl-, 2-methyl-3-butyl-, 2,4-dimethyl-, 2-methyl-4-ethyl-, 2-phenyl-4-methyl-, 2,3,4-trimethyl-, 2,3,4-triethyl- and especially, because of its ready accessibility, 2-methyl-2,5-dioxo-1,2-oxa-phospholane.

When $c^{K,PL}$ moles of the phospholane type are present in the reaction mixture, they also fall under the general definition of the core groups [—O—K—]$_c$K, when, for example, specifically $c^{K,PL}$=1 to $c^K$-1 times K$^{PL}$ which is

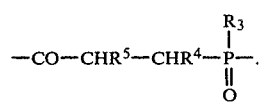

However, the phospholanes (III$_{PL}$) may never be employed as the sole core groups. At least one radical K$^P$ must always be present. In order to be able appropriately to characterize the different types of true organic phosphorus anhydrides, it is advisable to indicate the values of h, g and i as a subscripted index. This also applies in the case of the compounds from which they are formed.

The phosphonic acid anhydrides, which are also suitable, have the general formula

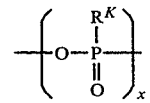

and the characteristic III$_{ho, go, io}$.

n is O and g and i in the term K$^P$ are both O. In this case and in the following formulae, x represents the degree of polymerization, which is not known in the case of the above formula. It is assumed that at room temperature these compounds are present partly as open-chain anhydrides (III$_{OF}$) and partly as cyclic anhydrides (III$_{CY}$). Compounds which can be employed are, for example, methane-phosphonic acid anhydride, propane-phosphonic acid anhydride, n-butane-phosphonic acid anhydride, isobutane-phosphonic acid anhydride, n-pentane-phosphonic acid anhydride, chloromethane-phosphonic acid anhydride, 1-chloroethane-phosphonic acid anhydride, 2-chloroethane-phosphonic acid anhydride, 2,3-dibromo-propane-phosphonic acid anhydride, vinyl-phosphonic acid anhydride and propene-2-phosphonic acid anhydride, preferably methane-, ethane- and propane-phosphonic acid anhydride.

Other true organic phosphorus anhydrides, which formally are proton-free, of the general formula:

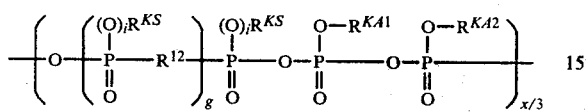

($III_{ho,g,i}$) are generally formed from one mole of a proton-free core ester donor ($KED_F$) of the general formula

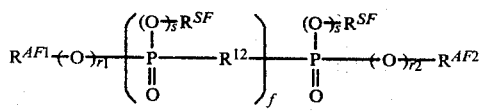

and one mole of phosphorus pentoxide. In the donor, $R^{AF1}=R^{AB1}$, apart from hydrogen, and $R^{SF}$ and $R^{AF2}=R^1$. Furthermore, in this case: $R^{KS}=R^1$, $R^{KA1}=R^{AF1}$ and $R^{KA2}=R^1$.

If, in the general term for $K^P$, g is 0 and I is 1, the compounds are alkyl metaphosphates. In comparison with polyphosphates according to U.S. Pat. No. 2,402,703, they are very inexpensive and easily obtainable by heating 1 mole of a tri-alkyl phosphate of the general formula

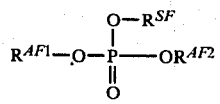

(and the characteristic $KED_{fo, rl, sl}$) and one mole of phosphorus pentoxide. In the ideal case, they correspond to the formula

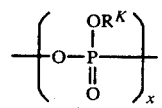

(and the characteristic $III_{ho,go,il}$). In this formula, $R^K$ can be either $R^{AF1}$, $R^{SF}$ or $R^{AF2}$.

The metaphosphates ($III_{ho,go,il}$) likewise also contain a proportion of the cyclic structures ($III_{CY}$) alongside open-chain structures ($III_{OF}$). Above all when $R^K$ is not $CH_3$, they have a much lower stability to heat than the phosphonic acid anhydrides. Above 80°–100° C., the higher esters decompose with the elimination of olefins. (Compare U.S. Pat. No. 2,402,703, page 1, column 1, line 14). The reaction with alcohols (II) and subsequently with alkylene oxides ($IV_o$) however already proceeds smoothly at, for example, 60°–90° C. Therefore, isoamyl methaphosphate, n-butyl metaphosphate, n-propyl metaphosphate, ethyl metaphosphate and methyl metaphosphate, which are obtainable from the corresponding trialkyl phosphates ($KED_{fo,rl,sl}$) and phosphorus pentoxide, are very suitable as compounds $III_{EC}$.

True organic mixed anhydrides which at the same time contain phosphonic acid anhydride groups and metaphosphoric acid ester groups, assume an intermediate position between phosphonic acid anhydrides and metaphosphates. According to U.S. Pat. No. 2,596,679 they are formed—presumably in addition to corresponding closed mixed polyesters—when 1 mole of the core ester donors, which comprise dialkyl alkanephosphonates of the formula

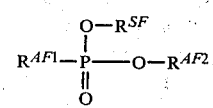

(and the characteristic $KED_{fo, rl/2, sl}$) is heated with 1 mole of phosphorus pentoxide at about 80° C. for a relatively long time. These compounds have the idealized general formula

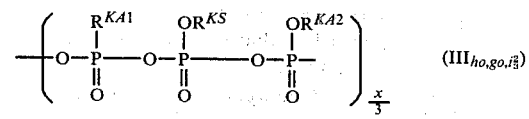

in which the radicals $R^{KA1}$ (i=0!) are bonded direct to the phosphorus and the radicals $R^{KS}$ and $R^{KA2}$ (i=1!) are bonded to the phosphorus via the oxygen. $R^{KA1}$ and $R^{KS}$ and $R^{KA2}$ are usually different. $R^{KA1}=R^{AF1}$, $R^{KA2}=R^1$, $R^{KS}=R^{SF}=R^1$ and f=g. The index g in the $K^P$ in this case is likewise nought, i is x/3 times 0 and 2x/3 times 1 and on average ⅔. Because of the ester radicals which they contain, true mixed anhydrides ($III_{ho,go,i2/3}$) of this type are-especially when $R^K$ is not $CH_3$—equally as unstable to heat above 80° C. as the metaphosphates. Nevertheless, the organic true mixed anhydrides ($III_{ho,go,i2/3}$) obtainable from 1 mole of phosphorus pentoxide and from, for example, 1 mole of diethyl n-butane-phosphate, di-isopropyl isobutane-phosphonate, diethyl n-propane-phosphonate, bis-(2-chloroethyl) n-propanephosphonate, dimethyl n-propane-phosphonate, di-n-butyl ethanephosphonate, diethyl ethane-phosphonate, dimethyl 2-cyano-ethane-phosphonate, bis-(2,3-dibromopropyl) ethanephosphonate, dimethyl methanephosphonate and the like, are also very suitable—especially because they are inexpensive—when alkylene oxides ($IV_o$) are used as the oxalkylating agent.

Further phosphorus anhydrides ($III_{Ec}$), which at least formally are true phosphorus anhydrides, are derived from phosphorus acids containing two phosphorus atoms per molecule, for which g is 1 in the term for $K^P$. If, at the same time, i is 0, the compounds are true a,ω-alkane-bis-(alkyl-phosphinic acid) anhydrides of the general formula

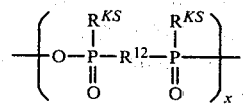

(and the characteristic $III_{ho,gl,i0}$)

Suitable compounds amongst these are, for example, 1,10-decane-bis-(methyl-phosphinic acid) anhydride, 1,6-hexa-n-bis-(ethyl-phosphinic acid) anhydride, 1,4-butane-bis-(methylphosphinic acid) anhydride, 1,2-ethane-bis-(methyl-phosphinic acid) anhydride and methane-bis-(methyl-phosphinic acid) anhydride.

If $g=1$ and $i=1$, the compounds are oligomeric compounds of the general formula

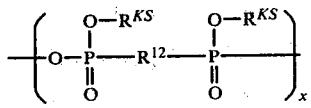

(and the characteristic $III_{h0,gl,il}$) which can be designated as dialkyl α,ω-alkane-meta-diphosphonates. Compounds of this category which can be used are, for example: diethyl 1,10-decane-meta-di-phosphonate, dimethyl 1,6-hexane-meta-di-phosphonate, diethyl 1,4-butane-pyro-di-phosphonate, di-n-butyl 1,2-ethane-meta-di-phosphonate, di-methyl 1,2-ethane-meta-di-phosphonate, di-methyl methane-meta-di-phosphonate, di-isopropyl methane-meta-di-phosphonate and the like, especially diethyl 1,2-ethane-meta-di-phosphonate, which is readily accessible.

True organic mixed anhydrides ($III_{EC}$) between phosphorus acids containing one phosphorus atom per molecule and containing two phosphorus atoms per molecule result, for example, when esters of a phosphonic or phosphinic acid containing two P atoms per molecule are heated with one mole of phosphorus pentoxide. In these mixed anhydrides ($III_{EC}$), g is 1/3 in each case. Thus, for example, true mixed anhydrides of the idealized general formula

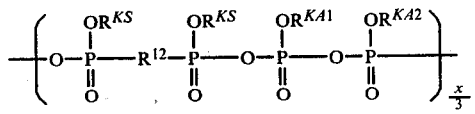

(and the characteristic $III_{h0,\,gl/3,il}$) are formed by heating 1 mole of the core ester donors, which comprise tetra-alkyl α,ω-alkane-pyro-phosphonates of the formula

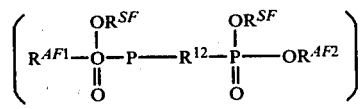

(and the characteristic $KED_{fl,rl,sl}$) with 1 mole of phosphorus pentoxide.

Suitable starting esters of the type $KED_{fl,rl,sl}$ are, for example, tetraethyl 1,6-hexane-di-phosphonate, tetramethyl 1,4-butane-di-phosphonate, tetraethyl 1,2-ethane-di-phosphonate, tetramethyl 1,2-ethane-di-phosphonate and the like, and preferably tetraethyl methane-di-phosphonate and tetramethyl methane-di-phosphonate.

Similarly suitable true mixed anhydrides ($III_{EC}$) of the idealized general formula

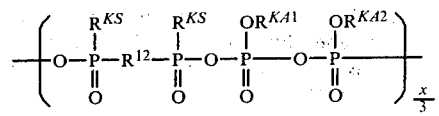

(and the characteristic $III_{h0,gl/3,il/2}$) are formed analogously, for example by heating 1 mole of phosphorus pentoxide with, in each case, one mole of the core ester donors comprising α,ω-alkane-bis-(alkylphosphinic acid alkyl esters) of the formula

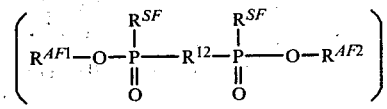

(and the characteristic $KED_{fl,rl,s0}$)

Examples of the latter compounds which may be mentioned are: 1,6-hexane-bis-(methyl-phosphinic acid iso-butyl ester), 1,2-ethane-bis-(methyl-phosphinic acid n-butyl ester), 1,2-ethane-bis-(methyl-phosphinic acid ethyl ester), methane-bis-(methyl-phosphinic acid ethyl ester) and the like.

The true organic phosphorus anhydrides ($III_{EC}$) illustrated in more detail above must always be proton-free. Terminated organic phosphorus anhydrides ($III_{AG}$), which can be employed, must contain at least two ($c=2$) anhydride equivalents. They correspond to the general formula III, in which, specifically, h must be 1. Proton-containing terminated organic phosphorus anhydrides ($III_{AG,H}$), in which at least one of the radicals $R^{AB}$ or $R^{SB}$ must be hydrogen, are always formed from true organic phosphorus anhydrides ($III_{EC}$) when $c^K$ anhydride equivalents of proton-free true open-chain organic phosphorus anhydrides ($III_{EC,OF}$) and/or cyclic organic phosphorus anhydrides ($III_{EC,CY}$) are mixed with proton-containing outer group donors ($AD_H$). For the general composition of the end reaction mixture I it is immaterial whether the outer group donors ($AD_H$) react chemically with the compounds $III_{EC}$ or not, that is to say whether a molecule or physical mixtures are present. The two outer groups (—OH and $R^{AB1}$—O—$_{r^-}$ $lA^B$) in the terminated starting anhydride ($III_{AG,H}$) are produced by the outer group donors ($AD_H$). The resulting proton-containing terminated anhydrides ($III_{AG,H}$) can generally be characterized by the formula

          ($III_{AG,H}$)

and by $III_{H,hl,r,s,i,f,g}$. For all meanings of $A^K$ (or $A^P$ and $A^{PL}$), proton-containing outer group donors ($AD_H$) which can be used and which optionally in each case can split one anhydride equivalent are water and acid esters or acids of phosphorus, of the general formulae

          ($AD_H$)

or, after inserting $A^B$ more specifically,

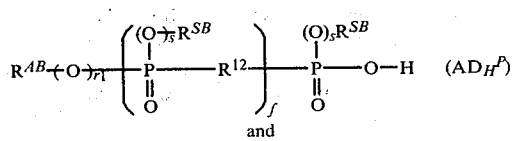

and

-continued

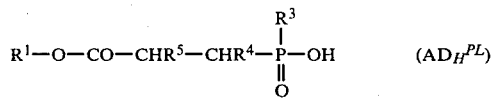 (AD$_H^{PL}$)

All the symbols used here again have the meaning indicated when illustrating the compounds I. If ÄZ$_{III,EC}$ is the equivalent number of the anhydride equivalents of true anhydrides (III$_{EC}$) employed and HÄZ$_{ADH}$ is the hydrogen equivalent number of proton-containing outer group donors (AD$_H$), HÄZ$_{ADH}=1$ to $c^{K,EC}/2$ hydrogen equivalents of proton-containing outer group donors (AD$_H$) can be added to the true anhydrides III$_{EC}$. The number of anhydride equivalents ($C^{K,AG}$) in the resulting proton-containing terminated phosphorus anhydride (III$_{AG,H}$) is then given by $$c^{K,AG} = (\text{ÄZ}_{III,EC}/\text{HÄA}_{AD,H})$$

Specific groups of proton-containing outer group donors (AD$_H$), which can convert proton-free true organic phosphorus anhydrides (III$_{EC}$) into proton-containing terminated anhydrides (III$_{AG,H}$) can generally again be characterized by adding the numerical values to the indices.

Donors which can be used are, for example, all acid alkanephosphonic acid derivatives of the formula

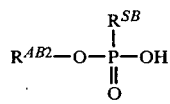

(and the characteristic AD$_{H,f0,rl,s0}$) such as, for example, methane-, ethane-, propane- and n-butane- phosphonic acid and monomethyl methane-phosphonate, monoethyl ethane-phosphate, monomethyl n-propane-phosphonate, monoethyl n-propane-phosphonate and the like, and also all acid α,ω-alkane-diphosphonic acid derivatives of the formula

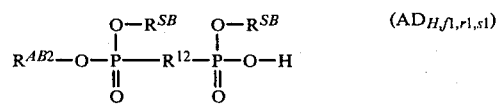 (AD$_{H,f1,rl,s1}$)

such as, for example, methane-, 1,2-ethane-, 1,4-butane-, 1,6-hexane- and 1,10-decane-di-phosphonic acid and their mono-, di- and tri-methyl, -ethyl, -isopropyl, -n-butyl and -n-pentyl esters and the like, and also all dialkyl-phosphinic acids of the formula

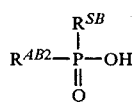

(and the characteristic AD$_{H,f0,rl/2,s0}$) such as, for example, dimethyl-phosphinic acid, methyl-ethylphosphonic acid, methyl-propyl-phosphinic acid, di-ethylphosphinic acid, di-n-butyl-phosphinic acid and the like, and also all acid α,ω-alkane-bis-(alkyl-phosphinic acid) derivatives of the formula

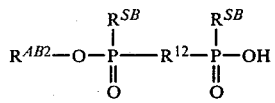

(and the characteristic AD$_{H,f1,rl,s0}$) such as, for example, methane- or ethane-, 1,4-butane-, 1,6-hexane- and 1,10-decane-bis-(methyl- or ethyl- or n-propylphosphonic acid) or their mono-methyl or -ethyl, -iso-propyl or -n-butyl esters and the like, and also all acid phosphoric acid derivatives of the formula

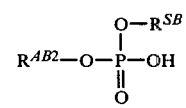

(and the characteristic AD$_{H,f0,rl,si}$) such as, for example, phosphoric acid and its mono- or dimethyl, -ethyl, -iso-propyl, -n-butyl or -iso-amyl esters and the like.

All proton-free or proton-containing organic anhydrides of the general formula

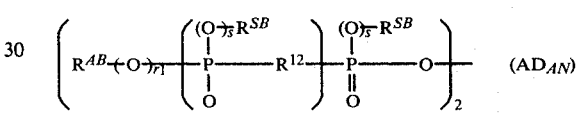 (AD$_{AN}$)

can be designated as anhydride outer group donors (AD$_{AN}$).

If AMZ$_{AD,AN}$ denotes the anhydride mole number of anhydride outer group donors (AD$_{AN}$), AMZ$_{AD,AN}=1$ to $c^{K,EC}$ moles of AD$_{AN}$ can likewise be reacted with the true anhydrides (III$_{EC}$) to give terminated anhydrides (III$_{AG}$).

Donors which can be used are, for example, all alkanepyro-phosphonic acid derivatives of the formula

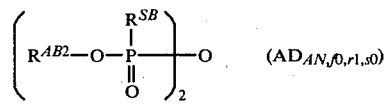 (AD$_{AN,f0,rl,s0}$)

such as, for example, methane-, ethane-, n-propane- and isobutane-pryo-phosphonic acid and their mono- or di-methyl -ethyl, -n-propyl and -n-butyl esters and the like, and also all dialkyl-phosphinic acid anhydrides of the formula

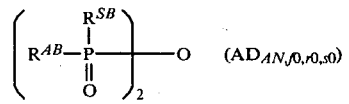 (AD$_{AN,f0,r0,s0}$)

such as, for example, dimethyl-, methyl-ethyl-, diethyl-, diisopropyl- and di-n-butyl-phosphinic acid anhydride and the like, and also all α,ω-alkane-pyro-di-phosphonic acids and esters of the general formula

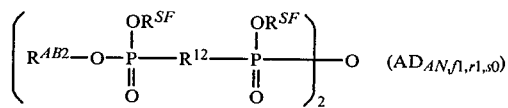

such as, for example, methane-, 1,2-ethane-, 1,3-propane- and 1,6-hexane-pyro-diphosphonic acid and their mono- or dimethyl or -ethyl, -isopropyl and -n-butyl esters and the like, and also all α,ω-alkane-pyro-bis-(alkyl-phosphinic acids) and their esters of the general formula

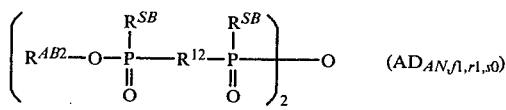

such as, for example, methane- (or 1,2-ethane-, 1,4-butane- or 1,10-decane-)pyro-bis-(methyl- (or ethyl-, isopropyl- or n-butyl-)phosphinic acid) or their methyl (or ethyl, n-propyl or n-butyl) esters and the like, and also pyro-phosphoric acid and its esters, of the general formula

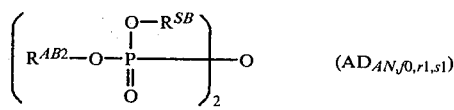

such, as, for example, pyrophosphoric acid and its mono-, di-, tri- or tetra-methyl (or -ethyl, -isopropyl, -n-butyl or -n-pentyl) esters and the like.

All anhydrides $AD_{AN}$, which act as outer group donors, increase the total number of all anhydride equivalents by $c^A=1$ to a total of $c=c^K+c^A=C^K+1$.

Another very practicable process for the manufacture of terminated proton-free organic phosphorus anhydrides of the general formula

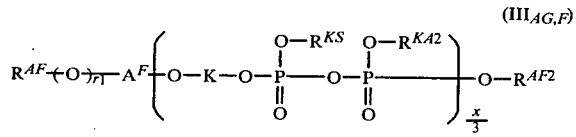   (III$_{AG,F}$)

comprises, quite generally, reacting the proton-free core ester donors of the general formula

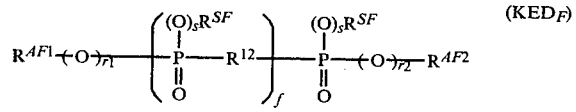   (KED$_F$)

with phosphorus pentoxide, not—as described above—in a molar ratio of 1:1 but in a molar ratio of 1.001 to 2.0:1 (compare also again U.S. Pat. No. 2,402,703 and 2,596,679). In these cases, the proton-free core ester donors (KED$_F$) do not only produce $c^K$ core ester groups of the idealized formula

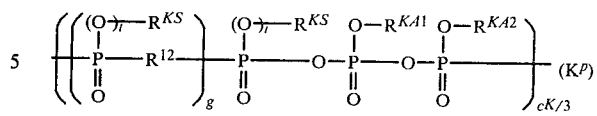

in which $R^{KS}=R^{SF}=R^1$, $R^{KA1}=R^{AF1}$ and $R^{KA2}=R^{AF2}=R^1$. In this case, the KED$_F$ at the same time also act as proton-free outer group donors (AD$_F$), so that h becomes 1 and two outer groups are formed—generally expressed—

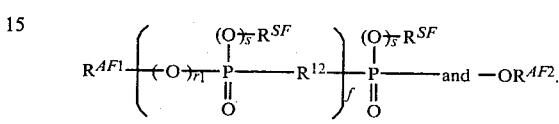

For all molar ratios $$MR = \frac{MZ_{KED,F}}{MZ_{PO}} = \frac{\text{mole number } KED_F}{\text{mole number phosphorus pentoxide}},$$

which are between 1.001 and 2.0, $c^K=3/MR$-1 core groups (K$^P$), and thus the same number ($c^K$) of anhydride equivalents, are also always formed in addition to the two outer groups, at the same time, per mole of the resulting oligomeric terminated proton-free organic phosphorus anhydride (III$_{AG,F}$).

The batch anhydride equivalents (AA) actually present in a particular batch are of great importance for all batch calculations. They are three times the batch mole number for phosphorus pentoxide (AMZ$_{PO}$). Thus, AA is always 3.AMZ$_{PO}$.

For a given batch mole number for phosphorus pentoxide (AMZ$_{PO}$), the batch mole numbers (AMZ$_{III,AG,F}$) for compounds III$_{AG,F}$ are the greater, the greater is the molar ratio minus 1 (MR-1) and thus the smaller is $c^K$. However, they also increase with AMZ$_{PO}$. Therefore, formally: AMZ$_{III,AG,F}$=(MR-1).AMZ$_{PO}$.

The proton-free terminated organic phosphorus anhydrides (III$_{AG,F}$) can be manufactured considerably more easily in practice, when, for example, MR is 1.1, than can the corresponding true anhydrides (III$_{EC}$), for which MR is 1.0. the solubility of phosphorus pentoxide in the core ester donors (KED$_F$) becomes increasingly poorer the closer the molar ratio approaches the limiting value of 1.0, since the viscosity also increases greatly. The MR range preferred in practice is therefore not at 1.0 but at about 1.05 to 1.50, or at $c^K$ values of 60 to 6. In order to achieve a uniform molecular weight distribution, mixtures, of this type, of P$_2$O$_5$ and the core ester donors (KED$_F$) should be heated at about 60°–90° C. for about 2-48 hours and preferably 6-20 hours. Alkenes must not be formed. All of the specific proton-free core ester donors (KED$_F$) which have already been mentioned for the manufacture of the corresponding true anhydrides (III$_{EC}$), that is to say all of the phosphoric acid esters mentioned, are also suitable for the manufacture of the oligomeric terminated proton-free organic phosphorus anhydrides (III$_{AG,F}$) if they are reacted with phosphorus pentoxide in a molar ratio of between 1.001 and 2.0.

In the same way as all true anhydrides (III$_{EC}$) are converted to proton-free terminated phosphorus anhydrides (III$_{AG,F}$) by proton-containing outer group donors (AD$_H$), the proton-free terminated phosphorus anhydrides (III$_{AG,F}$) can also be converted to shorter-chain proton-containing terminated phosphorus anhydrides (III$_{AG,H}$) by proton-containing outer group donors (AD$_H$). The latter anhydrides are also suitable as anhydrides (III) if they contain at least c=2 anhydride equivalents.

It must be emphasized that, for example, because all of the true organic phosphorus anhydrides (III$_{EC}$), including, for example, the alkane-phosphonic acid anhydrides (III$_{hO,gO,iO}$) and α, ω-alkane-bis-(alkyl-phosphonic acid) anhydrides (III$_{hO,gl,iO}$), which can be prepared as relatively very pure and single compounds, are highly hygroscopic, it is virtually impossible to react completely pure true anhydrides (III$_{EC}$) with the alcohols (II) and the oxalkylating agents (IV). In addition, the alcohols and the oxalkylating agents (IV) in industrial practice also always contain at least traces of water. Furthermore, especially at relatively high reaction temperatures and with relatively long reaction times, more or less pronounced yellow or brown colorations always arise in the reaction mixtures. These are due, at least in part, to slight dehydrations. Outer groups are also produced by alkaline catalysts. Therefore, the present application also includes all the end reaction compounds (I) for which b=0 and e is very small and the outer group protons of the anhydrides (III$_{AG,H}$) originate only from, for example, water impurities. For the above reasons, the hydroxyl numbers found in practice for the neutral end products (I$_{m,q0}$) are always greater than those calculated from the number of alcohol groups added (b.n) and the number of acid equivalents (e) in the compounds (III$_{AG,H}$). Furthermore, for the same reasons hydroxyl numbers are found for the end reaction mixtures (I) even when there are intentionally no alcohols (II) present (b=0) and no protons present (e=0) in the anhydrides (III)—although these hydroxyl numbers are low, for example 10. They originate in part from the catalysts. However, they are also found to a slight degree even when catalysts are absent. Accordingly, the batch mole number (AO) of oxalkylating agents (IV) necessary for the manufacture of neutral end products is virtually always greater than that calculated theoretically from the batch anhydride equivalent number (AA) and the batch proton equivalent number (AH)—in accordance with AO$_{TH}$=AA+AH.

(A) POSSIBILITIES FOR THE MANUFACTURE OF THE VARIOUS SUITABLE TYPES OF ORGANIC PHOSPHORUS ANHYDRIDES (III).

I. "True" organic phosphorus anhydrides (III$_{EC}$) (with h=0)

(1) 2-Alkyl-2,5-dioxo-1,2-oxa-phospholanes (III$_{PL}$) (German Patent Application No. P 25 26 689.1)

(2) Alkanephosphoric acid anhydrides (III$_{ho, go, io}$) compare Houben-Weyl Volume XII/1, pages 612–613.

(3) Metaphosphates (III$_{ho, go, il}$) compare Houben-Weyl Volume XII/2, page 939.

They are obtained specifically in accordance with U.S. Pat. No. 2,402,703 by heating 1 mole of P$_2$O$_5$ with 1 mole of the core ester donors

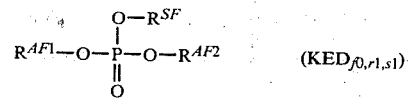

(=tri-alkyl phosphates).

(4) Mixed anhydrides containing alkane-phosphonic acid anhydride groups and metaphosphoric acid ester groups (III$_{ho,go,i2/3}$). They are obtained in accordance with U.S. Pat. No. 2,596,679 by heating 1 mole of P$_2$O$_5$ with 1 mole of the core ester donors

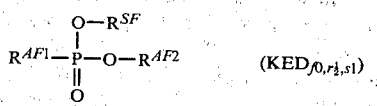

(=dialkyl alkane-phosphonates).

(5) Bis-(methyl-phosphonic acid) anhydrides (III$_{ho,gl,io}$). They are obtained by reacting bis-phosphonic acid derivatives of the formula

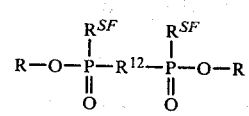

in which R denotes hydrogen, monovalent cations, the ammonium group or optionally halogen-substituted alkyl groups, with inorganic acid chlorides and/or phosgene and/or oxalyl chloride or with the corresponding bromine compounds, in a molar ratio of about 1:1 at temperatures of between about room temperature and 250° C., preferably of between about 100° and 200° C., optionally in the presence of inert solvents.

(6) Dialkyl α, ω-alkane-meta-di-phosphonates (III$_{ho,gl,il}$). They are manufactured analogously to the anhydrides described under (5), using tetraalkyl, α, ω-alkane-diphosphonates as the starting materials, so that 2 alkyl radicals are still retained.

(7) Mixed anhydrides containing α, ω-alkane-pyro-di-phosphonic acid di-alkyl ester groups and meta-phosphoric acid ester groups (III$_{ho,gl/3,il}$). These have not previously been described. They are obtained analogously to U.S. Pat. No. 2,596,679 by heating 1 mole of P$_2$O$_5$ with 1 mole of the core ester donors

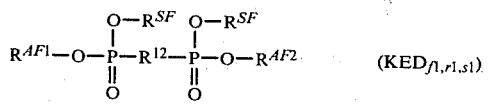

(=tetra-alkyl α, ω-alkane-di-phosphonates).

(8) Mixed anhydrides containing α, ω-alkane-bis-(alkylphosphonic acid) anhydride groups and meta-phosphoric acid ester groups (III$_{ho,gl/3,il/2}$).

These have not previously been described. They are obtained analogously to U.S. Pat. No. 2,596,679 by heating 1 mole of P$_2$O$_5$ with 1 mole of the core ester donors $$R^{AF1}-O-\overset{R^{SF}}{\underset{\underset{O}{\|}}{P}}-R^{12}-\overset{R^{SF}}{\underset{\underset{O}{\|}}{P}}-O-R^{AF2} \quad (KED_{fl,r1,s0})$$

($=\alpha, \omega$-alkane-bis-(alkyl-phosphonic acid alkyl esters).

II Terminated organic phosphorus anhydrides (III$_{AG}$) (with h=1)

(1) Proton-containing terminated organic phosphorus anhydrides (III$_{AG,H}$) with the general characteristic III$_{H,hl,r,s,i,f,g}$). They are formed from the 8 categories of true organic phosphorus anhydrides (III$_{EC}$) by stirring for 5 to 60 minutes (at 20°–150° C., preferably 40° to 90° C.) with HÄZ$_{ADH}$=1 to c$^{K,EC}$/2 moles of proton-containing outer group donors (AD$_H$) from the following 5 categories of compounds (with the characteristics indicated in brackets) which are known from the literature.

(a) Optionally substituted derivatives of dialkyl-phosphinic acids of the formula $$R^1-O-CO-CHR^5-CHR^4-\overset{R^3}{\underset{\underset{O}{\|}}{P}}-OH \quad (AD_{H,PL}) \text{ or}$$

$$R^{AB1}-\overset{R^{SB}}{\underset{\underset{O}{\|}}{P}}-OH \quad (AD_{H,f0,r0,s0}),$$

(b) Alkanephosphonic acid derivatives $$R^{AB2}-O-\overset{R^{SB}}{\underset{\underset{O}{\|}}{P}}-OH \quad (AD_{H,f0,r1,s0}),$$

(c) $\alpha, \omega$-Alkane-di-phosphonic acid derivatives $$R^{AB2}-O-\overset{O-R^{SB}}{\underset{\underset{O}{\|}}{P}}-R^{12}-\overset{O-R^{SB}}{\underset{\underset{O}{\|}}{P}}-OH \quad (AD_{H,fl,r1,s1}),$$

(d) $\alpha, \omega$-Alkane-bis-(alkyl-phosphonic acid) derivatives $$R^{AB2}-O-\overset{R^{SB}}{\underset{\underset{O}{\|}}{P}}-R^{12}-\overset{R^{SB}}{\underset{\underset{O}{\|}}{P}}-OH \quad (AD_{H,fl,r1,s0}), \text{ and}$$

(e) Phosphonic acid derivatives $$R^{AB2}-O-\overset{O-R^{SB}}{\underset{\underset{O}{\|}}{P}}-OH \quad (AD_{H,f0,r1,s1})$$

If all the combination possibilities are exhausted, a total of 8.5=40 different types of proton-containing terminated phosphorus anhydrides (III$_{AG,H}$) can be formed. A general picture of all of these compounds can be obtained with ease, if necessary, by means of a simple matrix and all the compounds can be classified by unequivocal group characteristics.

(2) Organic phosphorus anhydrides (III$_{AG,AN}$) terminated by anhydrides and having the general characteristic (III$_{AN,hl,r,s,i,f,g}$).

They contain a total number of anhydride equivalents which is 1 higher. They are formed from the 8 categories of true organic phosphorus anhydrides (III$_{EC}$) by stirring for 1 to 20 hours at 20° to 180° C., preferably 50° to 150° C., with AMZ$_{AD,AN}$=1 to c$^{K,EC}$ moles of anhydride outer group donors (AD$_{AN}$).

Such donors can be (f) Optionally substituted di-alkyl-phosphinic acid anhydrides of the formulae $$\left(R^1-OCO-CHR^5-CHR^4-\overset{R^3}{\underset{\underset{O}{\|}}{P}}-O\right)_2 \quad (AD_{AN,PL}) \text{ or}$$

$$\left(R^{AB1}-\overset{R^{SB}}{\underset{\underset{O}{\|}}{P}}-O\right)_2 \quad (AD_{AN,f0,r0,s0})$$

(g) Alkane-pyro-phosphonic acid derivatives $$\left(R^{AB2}-O-\overset{R^{SB}}{\underset{\underset{O}{\|}}{P}}-O\right)_2 \quad (AD_{AN,f0,r1,s0})$$

(h) $\alpha, \omega$-Alkane-pyro-di-phosphonic acid derivatives $$\left(R^{AB2}-O-\overset{O-R^{SB}}{\underset{\underset{O}{\|}}{P}}-R^{12}-\overset{O-R^{SB}}{\underset{\underset{O}{\|}}{P}}-O\right)_2 \quad (AD_{AN,fl,r1,s1})$$

(i) $\alpha, \omega$-Alkane-pyro-bis-(alkyl-phosphonic acid) derivatives $$\left(R^{AB2}-O-\overset{R^{SB}}{\underset{\underset{O}{\|}}{P}}-R^{12}-\overset{R^{SB}}{\underset{\underset{O}{\|}}{P}}-O\right)_2 \quad (AD_{AN,fl,r1,s0})$$

and (j) Pyro-phosphoric acid derivatives $$\left(R^{AB2}-O-\overset{O-R^{SB}}{\underset{\underset{O}{\|}}{P}}-O\right)_2 \quad (AD_{AN,f0,r1,s1})$$

If all the combination possibilities are exhausted, a total of, again, 8.5=40 different types of phosphorus anhydrides (III$_{AN}$) terminated by anhydrides can be formed. In the case of these compounds also, a general picture can be obtained with ease, if necessary, by means of a simple matrix and the compounds can be classified by unequivocal group characteristics.

(3) Proton-free terminated organic phosphorus anhydrides ($III_{AG,F}$) with the general characteristic ($III_{F,hl,r,s,i,f,g}$).

They are always formed—analogously to U.S. Pat. No. 2,596,679 when 1 mole of $P_2O_5$ is heated with 1.001 to 2.0 moles of proton-free core ester donors (KED). In each case 2 outer groups and $c^K = 3/MR - 1$ core groups ($K^P$) are formed per mole of $III_{AG,F}$.

In this case also - analogously to the manufacture of the corresponding true (always proton-free) organic phosphorus anhydrides with the characteristics $III_{ho,go,il}$ (=metaphosphates), $III_{ho,go,i2/3}$ (=mixed anhydrides containing, inter alia, alkane-phosphonic acid anhydride groups), $III_{ho,gl/3,il}$ (=mixed anhydrides containing, inter alia, $\alpha$, $\omega$-alkane-meta-di-phosphonic acid dialkyl ester groups) and $III_{h,gl/3,il/2}$ (=mixed anhydrides containing, inter alia, $\alpha$, $\omega$-alkane-bis-(alkyl-phosphonic acid) anhydride groups)—core ester donors (KED) with the following group characteristics can again be employed:

(a) $KED_{fo,rl,sl}$ (=trialkyl phosphates),
(b) $KED_{fo,rl/2,sl}$ (=dialkyl alkane-phosphonates),
(c) $KED_{fl,rl,sl}$ (=tetraalkyl $\alpha$, $\omega$-alkane-di-phosphonates) and
(d) $KED_{fl,rl,so}$ (=$\alpha$, $\omega$-alkane-bis-(alkyl-phosphinic acid alkyl esters).

There are, therefore, only four different "pure" types of proton-free terminated organic phosphorus anhydrides ($III_{AG,F}$) with the general characteristics $III_{F,hl,r,s,i,f,g}$.

To summarize, there is a total of 92 pure types of organic phosphorus anhydrides (III). They are 40 ($III_{AG,H}$)+40 ($III_{AG,AN}$)+4 ($III_{AG,F}$), that is to say a total of 84 different types of compound comprising terminated organic phosphorus anhydrides ($III_{AG}$), and 8 types of compound comprising true organic phosphorus anhydrides ($III_{EC}$). All of the specific individual anhydrides ($III_{SP}$) corresponding to these can be employed as compounds III and manufactured relatively simply - as has been summarized. It is obvious that individual anhydrides of the 92 different pure types of anhydrides (III) can also be mixed with one another as desired without chemical reactions having to take place. All of these mixtures also fall under the general formula for the anhydrides (III).

For the specific batch calculation it suffices - even in the case of mixtures—to know as previously as possible the total number of anhydride equivalents present in the batch (AA). By freely choosing the mole number (b) of n-hydric alcohols or the batch proton equivalents (AH) in the anhydrides (III) it is possible—if AA is known—to pre-plan the properties of the resulting reaction mixtures (I) to a substantial extent. It is then possible, for example, easily to work towards a specific average side chain length—expressed by the index m—and thus towards a specific end hydroxyl number (or if q is 1 also a residual acid number). In general, the relationship which applies is $c = (m+1+q) \cdot (b \cdot n + e)$ and the particularly important rearrangement $m = c/b \cdot n + e - 1 - q$; $b \cdot n + e$ must be at least 1 and c must be at least 2. m may also be 0 but may not be negative. In practice, this means that, for example, formally—on average—after the reaction of the alcohols (II) with the anhydrides (III) no free alcohols groups may remain over which have not found a phosphorus anhydride equivalent as a reactant.

Oxalkylating agents of the formula

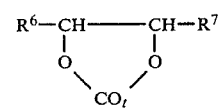

which can be used are, when t is 0, all alkylene oxides of the formula

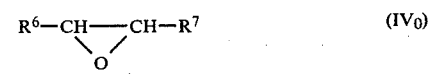

such as, for example, 1,2-butylene oxide, epichlorohydrin, propylene oxide and preferably ethylene oxide. When t is 1, the alkylene carbonates of the formula

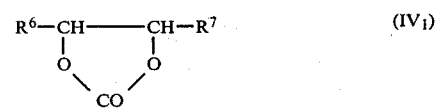

are suitable, such as, for example, propylene carbonate and preferably ethylene carbonate.

Especially when $g = 0$ and $b \cdot n$ and e are relatively very small and $c^K$ is relatively large and no alkaline catalysts are used, it is possible, when the compounds II, III and IV are reacted at relatively low temperatures (about $<100°$ C.), for a proportion of the undesired cyclic diester-type reaction products of type ($K_{IV}$), which are free from hydroxyl groups, to form first in some cases. In particular, the substituted 1,3-di-oxa-2-oxo-2-phospholanes

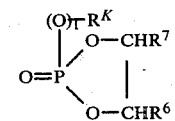

which in some cases arise as intermediate products and can form from phosphonic acid anhydride derivatives and meta- or polyphosphoric acid ester derivatives and only alkylene oxides after a side reaction has taken place, have the undesired property of being relatively readily volatile and of very easily undergoing hydrolysis with water, the ring being opened and acid end products being formed. (Compare J. of general Chemistry of the U.S.S.R., Volume 34, No. 4, pages 731–735 (1965)). Especially at higher temperatures (40°–200° C.) and in the presence of strongly alkaline catalysts, they react, after an after-treatment of about 1–20 hours, with the $b \cdot n + e$ hydroxyl groups which at least are already present in the reaction mixture. With opening of the ring, lengthening of the chain and an increase in the m value, the corresponding desired reaction compounds (I) result—discernible by the disappearance of the corresponding bands, a reduction in the sensitivity to water and an increase in the viscosity. However, even if slight residues of cyclic diesters ($K_{IV}$) are still present in the end product (I), these virtually do not impair the usefulness of the end reaction mixture (I), since, for example, acid pH values are in any case required for fixing the end compounds (I) on textile material with the aid of, for example, aminoplast precondensates. The after-treatment can therefore be carried out but does not have to be carried out in all cases.

The stability to heat of the organic phosphorus anhydrides (III) and of the intermediate products and end reaction products obtainable therefrom varies. Whenever the indices r and s, and above all s, are 1 and $R^{AB}$ and $R^{SB}$ are not hydrogen, side reactions can occur in some cases at higher temperatures. In such cases, it is therefore advisable to use alkylene oxides ($IV_O$), since, in general, these already react at lower temperatures than the alkylene carbonates ($IV_1$). Alkylene carbonates ($IV_1$) are advantageously employed above all when high-melting or higher-molecular alcohols (II) are used, when the reaction can not be carried out with, for example, ethylene oxide for safety reasons or when an additional end point control (evolution of $CO_2$) is desired.

The use of inert solvents or diluents is not necessary in most cases. However, it is also possible to add, for example, acetone, methyl ethyl ketone, acetonitrile, 1,2-dichloroethane, benzene, toluene, xylene or chlorobenzene, but above all dioxane—if necessary—as diluents or solubilizing agents, without adverse effect, and to remove these again by distillation, for example before the reaction with the oxalkylating agents (IV) has gone to completion or only at the very end of the reaction.

The temperatures for the reaction between the compounds II (b>0) and III are between 0° and 180° C. or higher, for example up to 250° C., preferably between 20° and 150° C. and especially 80° to 150° C. The reaction of the acid intermediate products obtained when b>0 or —when b is 0—of the proton-containing terminated phosphorus anhydrides ($III_{AG,H}$) with the 1,2-alkylene carbonates ($IV_1$) takes place at between about 80° and 240° C., preferably 150°–220° C. The alkylene oxides ($IV_O$) react at between 20° and 240° C., preferably 60°–180° C. The reaction can be carried out in stages and specifically, when b>0, by first reacting b moles of the alcohols (II) containing n alcoholic groups with b·n+e anhydride equivalents of the phosphorus anhydrides (III) and then allowing the oxalkylating agents (IV) to act, first in an amount of only b·n moles when e=0 and of at least b·n+e moles when e>0, on the reaction mixture until the acid number has fallen to virtually 0. The further equivalents of the phosphorus anhydrides (III) and of the oxalkylating agents (IV) are then added, alternately, up to the desired end amounts of, in total, $c=(b·n+e)·(m+1+q)$ equivalents of the anhydrides (III) and at least $u_N=(b·n+e)·(m+1+q)$ moles of the oxalkylating agents (IV), if neutral reaction mixtures (I) are to be obtained, or up to $N_{SF}=(b·n+e)·(m+1)$ moles of the oxalkylating agents (IV), when q is 1, that is to say products which are still acid are desired.

However, the embodiment preferred for b>0 is to mix all $c=(b·n+e)·(m+1+q)$ anhydride equivalents of the anhydrides (III) together with, in each case, b moles of the alcohols (II) containing n alcohol groups and—in order to obtain acid end products (q=1)—reacting the mixture with $(b·n+e)·(m+1)$ moles of the oxalkylating agents (IV), or, in order to obtain neutral end products (q=0), reacting the mixture with at least $(e+b·n)·(m+1+q)$ moles of the oxalkylating agents (IV). If they are alkylene carbonates ($IV_1$), the compounds (IV) can be admixed with the mixtures of II and III from the start. The same applies in the case of alkylene oxides ($IV_O$) of low volatility, such as, for example, epichlorohydrin. Readily volatile alkylene oxides ($IV_0$), such as, for example, propylene oxide or ethylene oxide, on the other hand, are added dropwise or introduced as a gas at the reaction temperatures. A similar procedure can be followed when b=0 and e>0, that is to say proton-containing terminated phosphorus anhydrides ($III_{AG,H}$) but no alcohols (II) are employed. The reaction of II and III is then, of course, omitted.

Depending on the numerical values of n, e and m and on which compounds $Z_n(-O-H)_n$ are present, the end products (I) are colorless or have a more or less pronounced yellowish color and are of different consistencies. If $n+e=1$ or 2, $R^{AB}$, $R^{SB}$ and $R^K$ each denote a lower alkyl radical and $R^4$ or $R^5$ either likewise denotes a lower alkyl radical or denotes hydrogen, g=0 and at least one of r, s and i denotes 1, the products are in the main viscous liquids, and when g=1 and $e+n>3$ and r, s and i=0 the products are in the main solid viscous masses; however all the products are readily soluble in water. If the molecular weight increases as a result of long alkyl radicals or long individual chains, that is to say as a result of high values for m, the viscosity in some cases increases considerably. The stability of the reaction products (I) to hydrolysis is the greatest when s and, above all, i are each O. It decreases when r, s and, above all, i are 1. On the other hand, these categories of compounds are accessible particularly inexpensively.

Long fatty radicals and aromatic base substances, even if they additionally also contain other groups which greatly reduce the solubility in water, such as, for example, the halogen atoms fluorine, chlorine and bromine, are water-soluble or dispersible in water at m values of above about 2-5.

Like the compounds of Applications Nos. P 25 56 482.3 (=HOE 75/F 316) and P 26 47 745.2 (=HOE 76/F 250), the resulting compounds of the formula I, especially the neutral and polyvalent compounds containing several hydroxyl groups and with m>1, are very suitable, because of their phosphorus content, which is relatively high throughout, as precursors for flameproofing agents or, in combination with crosslinking substances, also direct as wash-resistant fixable flameproofing agents, for example for textiles.

Because of their surface-active properties, the compounds containing long alkyl groups (of up to 18 C. atoms) can also be used as surface-active agents.

So that a general picture of the preparation examples illustrating the text can be obtained more easily, these examples have been subdivided in accordance with the nature of the anhydrides (III) used and in each case the general formula of the type of anyhydride and, in brackets, its characteristic have been indicated from the start.

Preference has been given to the tabular form because this gives a simple overall picture.

When carrying out the reactions in practice, one batch anhydride equivalent (AA=1) was always used at the start. When b was >0, correspondingly small fractions of moles (b) of n-hydric alcohols (II) of the formula $Z_n(OH)_n$ and of AH batch proton equivalents were employed. b and AH were always less than 1.

Only the number of moles of the batch oxalkylating agents (AO) was, for the abovementioned reasons, always somewhat greater than 1 for the neutral end products (with an acid number of >3).

To enable a general picture of the preparation examples to be presented in tabular form, it was necessary to convert all of the figures, i.e. to multiply them by the indicated batch anhydride equivalent number (AA). This resulted in mole numbers (b) for alcohols (II) of the formula $Z_n(OH)_n$ of 1 in each case. The number of batch alcohol group equivalents (b.n) was accordingly always=n.

The statements made all relate to the converted data. When no alcohols were present (b=0) the data were appropriately related to 1 mole of the anhydrides (III$_{AG}$), which may be terminated by the catalyst radicals only, with, in that case, c=AA batch anhydride equivalents and e=AH protons.

In all cases, the alcohols (II) were added to the anhydrides (III) at room temperature (25° C.) or at the liquefaction temperatures of any solid anhydrides (III), in the course of 1 to 30 minutes, with cooling if necessary. The different reaction conditions indicated therefore always relate only to the reaction with the oxalkylating agents (IV) carried out in the 2nd stage.

The acid numbers of all end reaction products, measured in mg of KOH per g, were <3. In Example 20, acid products were also characterized.

In Preparation Examples 1–9, 10b, 15, 19 and 20 b is >0 in each case and in 10b e is additionally <0. Examples 1–9, 10b, 15 and 19 describe the direct process (DP) and Example 20 describes the multi-stage process (MSP).

Preparation Examples 10a, 11–14 and 16–18, in which, in each case b=0 and e>0, illustrate the single stage process (SSP).

The further abbreviations which are used in the Tables and are not shown in the particular formulae of the types of anhydride (III) denote:

$Z_n$=hydrocarbon radical of the n-hydric alcohols
T=oxalkylation temperature in degrees centigrade
(N=after-treatment temperature in degrees centigrade)
Zt=oxalkylation time in hours (rounded up or down)
(NO=after-treatment time in hours)
Kat=catalyst (So=sodium carbonate, Po=potassium carbonate, NaHy=sodium hydroxide, NaM=sodium methylate, Tra=triethanolamine and NaML=33% strength solution of NaM in methanol) The figures denote mole per batch, N=aftertreatment
AA=batch anhydride equivalent number
AO=batch oxalkylating agent mole number (EO=ethylene oxide, PyO=propylene oxide, Ec=ethylene carbonate and Epi=epichlorohydrin)
m=average degree of oligomerization per chain
OHZ=hydroxyl number found (mg of KOH per g)
P=phosphorus content found in per cent by weight
$n_D^{20}$=refractive index at 20° C.
EP-MR=ester/phosphorus pentoxide molar ratio. It varies between 1.0 (always in Examples 2 and 3) and 2.0.
KS-MR=core anhydride/acid molar ratio. It is identical to $c^K$ and usually equal to AA
KAN-MR=core anhydride/(outer) anhydride molar ratio. It is identical to $c^K$.

PREPARATION EXAMPLES

EXAMPLE 1

Type of anhydride:

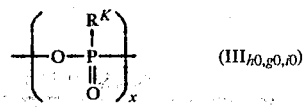 (III$_{h0,g0,i0}$)

| | $R^K$ | $Z_n$ | T | Zt | Kat | n | AA | AO | m | OHZ | P | $n_D$ |
|---|---|---|---|---|---|---|---|---|---|---|---|---|
| a | CH$_3$ | C$(\text{CH}_2)_4$ | 120 | 5 | 0.02 So | 4 | 8 | 9.1 EO | 1.0 | 222 | 21.3 | 1.4789 |
| b | CH$_3$ | n-C$_6$H$_{12}$ | 120 | 7 | 0.06 So | 2 | 6 | 7.8 PyO | 2.0 | 184 | 18.0 | 1.4690 |
| c | CH$_3$ | n-C$_6$H$_{12}$ | 115 | 8 | 0.04 So | 2 | 8 | 9.1 EO | 3.0 | 102 | 21.6 | 1.4792 |
| d | C$_2$H$_5$ | — | 130 | 3 | 1.0 So | 2 | 100 | 100 EO | 49 | 11 | 22.8 | 1.4781 |
| e | C$_2$H$_5$ | —C$_2$H$_4$— | 120 | 7 | 0.03 So | 2 | 6 | 6.5 EO | 2.0 | 143 | 20.7 | 1.4742 |
| f | C$_2$H$_5$ | n-C$_6$—H$_{12}$ | 110 | 8 | 0.04 So | 2 | 11 | 12.0 EO | 4.5 | 85 | 20.4 | 1.4761 |
| g | C$_2$H$_5$ | CH$_2$—CH—CH$_2$ | 95 | 6 | — | 3 | 9 | 10.4 EO | 2.0 | 151 | 20.2 | 1.4731 |
| h | C$_2$H$_5$ | CH$_2$—CH=CH—CH$_2$ | 130 | 3 | 0.12 So | 2 | 12 | 12.2 EO | 5.0 | 72 | 21.3 | 1.4762 |
| i | n-C$_3$H$_7$ | C$_2$H$_4$ | 110 | 3 | 0.05 So | 2 | 10 | 11.2 EO | 4.0 | 97 | 19.1 | 1.4682 |
| j | n-C$_3$H$_7$ | C$_2$H$_4$ | 120 | 4 | 0.06 So | 2 | 6 | 6.4 EO | 2.0 | 116 | 18.9 | 1.4700 |
| k | n-C$_3$H$_7$ | — | 130 | 6 | 1.0 So | 2 | 100 | 104 EO | 49 | 11 | 20.3 | 1.4633 |
| l | n-C$_3$H$_7$ | CH$_2$—CH—CH$_2$ | 130 | 10 | 0.04 So | 3 | 5 | 11.2 EO | 2.0 | 164 | 17.5 | 1.4718 |
| | | | 30N | 1N | 0.02 NaMIN | | | | | | | |
| m | n-C$_3$H$_7$ | C$(\text{CH}_2)_4$ | 100 | 3 | 0.07 | 4 | 12 | 12.8 EO | 2.0 | 116 | 18.7 | 1.4711 |
| n | n-C$_3$H$_7$ | C$(\text{CH}_2)_4$ | 190 | 6 | 0.18 So | 4 | 8 | 16 Ec | 3.0 | 86 | 14.2 | |
| o | n-C$_3$H$_7$ | C$(\text{CH}_2)_4$ | 100 | 6 | 0.06 So | 4 | 8 | 9.3 EO | 1.0 | 112 | 17.7 | 1.4689 |
| p | CH$_2$—CH | C$_2$H$_4$ | 110 | 7 | 0.03 So | 2 | 6 | 6.4 EO | 2.0 | 147 | 21.0 | 1.4916 |

EXAMPLE 2

Type of anhydride:

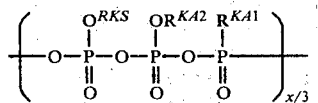 (III$_{h0,g0,i\frac{2}{3}}$)

| | $R^{KA1}$ | $R^{KS}=$ $=R^{KA2}$ | $Z_n$ | T | Zt | Kat | n | AA | AO (EO) | m | OHZ | P | $n_D$ |
|---|---|---|---|---|---|---|---|---|---|---|---|---|---|
| a | C$_2$H$_5$ | CH$_3$ | n-C$_6$H$_{12}$ | 140 | 4 | 0.15 So | 2 | 24.2 | 27.5 | 11.1 | 88 | 20.7 | 1.4550 |
| b | C$_2$H$_5$ | C$_2$H$_5$ | n-C$_6$H$_{12}$ | 90 | 5 | 0.03 So | 2 | 2.66 | 3.7 | 0.33 | 240 | 14.9 | 1.4608 |
| c | C$_2$H$_5$ | C$_2$H$_5$ | n-C$_6$H$_{12}$ | 90 | 6 | 0.08 So | 2 | 13.2 | 13.4 | 5.6 | 95 | 19.4 | |
| d | n-C$_3$H$_7$ | CH$_3$ | n-C$_6$H$_{12}$ | 88 | 7 | 0.02 So | 2 | 2.0 | 2.9 | 0 | 269 | 14.3 | 1.4611 |
| e | n-C$_3$H$_7$ | CH$_3$ | C$(\text{CH}_2)$ | 100 | 9 | 0.04 So | 4 | 4.0 | 6.0 | 0 | 309 | 16.0 | 1.4679 |

EXAMPLE 2-continued

Type of anhydride:

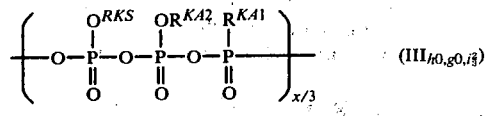

|   | $R^{KA1}$ | $R^{KS}=$ $=R^{KA2}$ | $Z_n$ | T | Zt | Kat | n | AA | AO (EO) | m | OHZ | P | $n_D$ |
|---|---|---|---|---|---|---|---|---|---|---|---|---|---|
| f | n-C$_3$H$_7$ | CH$_3$ | 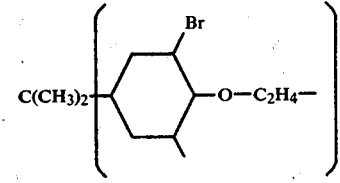 | 130 | 6 | 0.05 So | 2 | 6.0 | 6.6 | 2.0 | 74 | 11.7 | 1.5179 (40°) |

EXAMPLE 3

Type of anhydride:

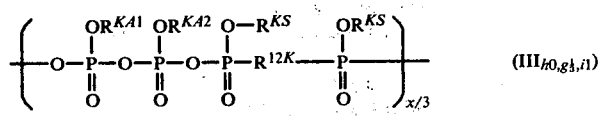

|   | $R^{12K}$ | $R^{KA1}$ | $R^{KS}$ $=R^{KA2}$ | $Z_n$ | T | Zt | Kat | n | AA | AO (EO) | m | OHZ | P | $n_D$ |
|---|---|---|---|---|---|---|---|---|---|---|---|---|---|---|
| a | CH$_2$ | C$_2$H$_5$ | P$_2$H$_5$ | C$\pm$CH$_2$)$_4$ | 90 | 10 | 0.04 So | 4 | 6 | 9.4 | 0.5 | 189 | 19.4 | too viscous |
| b | CH$_2$ | C$_2$H$_5$ | C$_2$H$_5$ | n-C$_6$H$_{12}$ | 80 | 14 | 0.03 SO | 2 | 4 | 4.6 | 1.0 | 154 | 20.6 | |

EXAMPLE 4

Type of anhydride:

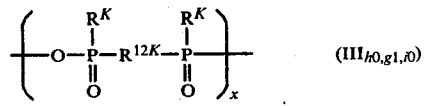

|   | $R^{12}$ | $R^K$ | $Z_n$ | T | Zt | Kat | n | AA | AO | m | OHZ | P | $n_D$ |
|---|---|---|---|---|---|---|---|---|---|---|---|---|---|
| a | CH$_2$ | CH$_3$ | C$_2$H$_4$ | 175 | 11 | 0.04 So | 2 | 3.2 | 4.0 Ec | 0.6 | 136 | 22.8 | too viscous |
| b | CH$_2$ | CH$_3$ | n-C$_6$H$_{12}$ | 180 | 6 | — | 2 | 8.0 | 12.3 EO | 3.0 | 157 | 27.5 | " |
| c | CH$_2$ | CH$_3$ | n-C$_4$H$_{12}$ | 145 | 10 | — | 2 | 10.0 | 12.0 EO | 4.0 | 28 | 24.6 | " |
| d | n-C$_2$H$_4$ | CH$_3$ | C$_2$H$_4$ | 150 | 5 | — | 2 | 4.0 | 4.2 EO | 1.0 | 137 | 26.6 | " |
| e | n-C$_2$H$_4$ | CH$_3$ | C$_2$H$_4$ | 140 | 4 | — | 2 | 6.0 | 6.5 EO | 2.0 | 99 | 27.1 | " |
| f | n-C$_2$H$_4$ | CH$_3$ | n-C$_6$H$_{12}$ | 140 | 21 | — | 2 | 5.0 | 6.1 PyO | 1.5 | 96 | 23.7 | " |
| g | n-C$_2$H$_4$ | CH$_3$ | n-C$_6$H$_{12}$ | 145 | 16 | 0.1 So | 2 | 10.0 | 12.1 PyO | 4.0 | 68 | 24.8 | " |
| h | n-C$_2$H$_8$ | CH$_3$ | n-C$_6$H$_{12}$ | 145 | 12 | — | 2 | 10.0 | 10.4 EO | 4.0 | 95 | 24.6 | " |
| i | n-C$_6$H$_{12}$ | CH$_3$ | — | 190 | 2 | 1.0 So | 2 (from sodium carbonate) | 1000 | 1200 Ec | 499 | 22 | 23.0 | " |
| j | n-C$_6$H$_{12}$ | CH$_3$ | CH$_3$ | 130 | 10 | — | 1 | 8.0 | 8.2 EO | 7.0 | 65 | 23.1 | " |
| k | n-C$_6$H$_{12}$ | CH$_3$ | n-C$_{18}$H$_{37}$ | 190 | 4 | 0.04 So | 1 | 4.0 | 4.4 Ec | 3.0 | 60 | 18.2 | 1.4854 (40°) |
| l | n-C$_6$H$_{12}$ | CH$_3$ | n-C$_6$H$_{12}$ | 150 | 6 | — | 2 | 8.0 | 9.3 EO | 3.0 | 175 | 22.3 | too viscous |
| m | n-C$_6$H$_{12}$ | CH$_3$ | n-C$_6$H$_{12}$ | 135 | 9 | — | 2 | 5.0 | 5.1 PyO | 1.5 | 79 | 19.2 | " |
| n | n-C$_6$H$_{12}$ | CH$_3$ | n-C$_6$H$_{12}$ | 130 | 10 | — | 2 | 8.0 | 9.0 EO | 3.0 | 78 | 21.4 | " |
| o | n-C$_6$H$_{12}$ | CH$_3$ | n-C$_6$H$_{12}$ | 165 | 4 | — | 2 | 16.0 | 16.6 EO | 7.0 | 186 | 22.6 | " |
| p | n-C$_6$H$_{12}$ | CH$_3$ | CH$_2$—CH—CH$_2$ | 170 | 5 | 0.09 So | 3 | 18.0 | 21.8 Ec | 5.0 | 89 | 22.5 | " |
| q | n-C$_6$H$_{12}$ | CH$_3$ | C$\pm$CH$_2$)$_4$ | 185 | 2 | 0.08 So | 4 | 8.0 | 10.0 Ec | 1.0 | 115 | 21.0 | " |
| r | n-C$_{10}$H$_{20}$ | CH$_3$ | C$\pm$CH$_2$)$_4$ | 180 | 2 | 0.2 So | 4 | 10.0 | 12.0 Ec | 1.5 | 68 | 17.8 | 1.4870 (40°) |
| s | n-C$_2$H$_4$ | CH$_3$ | C$\pm$CH$_3$)$_2$ | 145 | 14 | 0.04 So | 2 | 4.0 | 4.4 EO | 1.0 | 122 | 25.4 | too viscous |
| t | n-C$_6$H$_{12}$ | CH$_3$ | C$_6$F$_{13}$C$_2$H$_4$ | 110 | 8 | 0.03 So | 1 | 2.0 | 2.1 EO | 1.0 | 1 | 14.1 | 1.4476 |
| u | C$_2$H$_4$ | CH$_3$ | n-C$_6$H$_{12}$ | 115 | 4 | — | 2 | 5.0 | 6.9 Epi | 4.0 | 97 | 20.4 | too viscous |

EXAMPLE 5

Type of anhydride:

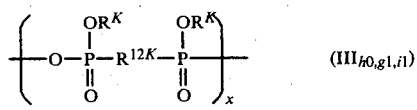 (III$_{h0,g1,i1}$)

| | R$^{12K}$ | R$^K$ | Z$_n$ | T | Zt | Kat | n | AA | AO (EO) | m | OHZ | P | n$_D$ |
|---|---|---|---|---|---|---|---|---|---|---|---|---|---|
| a | C$_2$H$_4$ | C$_2$H$_5$ | C$_2$H$_4$ | 100 | 2 | 0.08 So | 2 | 2.0 | 2.8 | 0 | 169 | 16.9 | 1.4730 |
| b | C$_2$H$_4$ | C$_2$H$_5$ | C$-$(CH$_2$)$_4$ | 140 | 5 | 0.08 So | 4 | 4.0 | 5.7 | 0 | 162 | 18.8 | 1.4829 |

EXAMPLE 6

Type of anhydride:

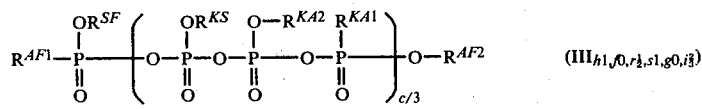 (III$_{h1,f0,r\frac{1}{2},s1,g0,i\frac{1}{3}}$)

| | R$^{AF1}$=R$^{KA1}$ | R$^{SF}$=R$^{AF2}$=R$^{KS}$=R$^{KA2}$ | EP–MR | c | Z$_n$ | T | Zt | Kat | n | AA | AO (EO) | m | OHZ | P | n$_D$ |
|---|---|---|---|---|---|---|---|---|---|---|---|---|---|---|---|
| a | C$_2$H$_5$ | C$_2$H$_5$ | 1.1 | 30 | n-C$_6$H$_{12}$ | 90 | 8 | 0.02 So | 2 | 2 | 2.9 | 0 | 240 | 14.4 | 1.4587 |
| b | C$_2$H$_5$ | C$_2$H$_5$ | 1.2 | 15 | n-C$_6$H$_{12}$ | 100 | 4 | 0.04 So | 2 | 6 | 7.2 | 2.0 | 138 | 17.7 | 1.4552 |
| c | C$_2$H$_5$ | C$_2$H$_5$ | 1.1 | 30 | C$-$(CH$_3$)$_2$ | 90 | 5 | 0.06 So | 2 | 6 | 6.2 | 2.0 | 149 | 18.7 | 1.4612 |
| d | C$_2$H$_5$ | C$_2$H$_5$ | 1.2 | 15 | C$-$(CH$_2$)$_4$ | 90 | 8 | 0.05 So | 4 | 7.5 | 7.6 | 0.9 | 159 | 17.6 | 1.4608 |
| e | C$_2$H$_5$ | C$_2$H$_5$ | 2.0 | 3 | C$-$(CH$_2$)$_4$ | 85 | 5 | 0.05 So | 4 | 7.5 | 7.5 | 0.9 | 105 | 17.8 | 1.4515 |
| f | n-C$_3$H$_7$ | CH$_3$ | 1.1 | 30 | 1,4-C$_4$H$_8$ | 65 | 10 | 0.02 So | 2 | 2 | 2.7 | 0 | 272 | 15.1 | 1.4592 |
| g | n-C$_3$H$_7$ | CH$_3$ | 1.04 | 75 | 1,6-C$_6$H$_{12}$ | 90 | 6 | 0.03 So | 2 | 4 | 4.9 | 1.0 | 169 | 17.1 | 1.4622 |
| h | n-C$_3$H$_7$ | CH$_3$ | 1.1 | 30 | C$-$(CH$_3$) | 100 | 3 | 0.06 So | 2 | 6 | 6.5 | 2.0 | 110 | 18.7 | 1.4566 |
| i | n-C$_3$H$_7$ | CH$_3$ | 1.1 | 30 | C$-$(CH$_2$)$_4$ | 120 | 6 | 0.1 So | 4 | 15 | 16.3 | 2.8 | 87 | 19.9 | 1.4648 |
| j | n-C$_3$H$_7$ | CH$_3$ | 2.0 | 3 | C$-$(CH$_2$)$_4$ | 100 | 5 | 0.08 So | 4 | 6 | 6.1 | 0.5 | 151 | 19.2 | 1.4569 |
| k | n-C$_3$H$_7$ | CH$_3$ | 1.1 | 30 | C$-$(CH$_2$)$_4$ | 90 | 8 | 0.16 So | 4 | 16 | 18.3 | 3.0 | 80 | 19.6 | 1.4610 |
| l | n-C$_3$H$_7$ | CH$_3$ | 1.04 | 75 | N$-$(C$_2$H$_4$)$_3$ | 6 | 120 | =Z$_n$ | 3 | 6 | 7.0 | 2.0 | 160 | 17.6 | |
| m | n-C$_3$H$_7$ | CH$_3$ | 1.04 | 75 | CH$_2$=C(CH$_3$)—CO—O—C$_2$H$_4$ | 60 | 8 | 0.04 So | 1 | 4 | 5.5 | 3.0 | 114 | 15.9 | |
| n | n-C$_3$H$_7$ | CH$_3$ | 1.04 | 75 | CH$_2$=C(CH$_3$)—CO—O—C$_2$H$_4$ | 60 | 16 | — | 1 | 2 | 3.2 | 1.0 | 172 | 13.2 | 1.4606 |
| o | C$_2$H$_5$ | CH$_2$=CH—CH$_2$ | 2.0 | 3 | C$-$(CH$_2$)$_4$ | 50 | 14 | 0.12 So | 4 | 12 | 14.2 | 2.0 | 87 | 17.2 | |
| p | n-C$_3$H$_7$ | C$_2$H$_5$ | 1.1 | 30 | N$-$(C$_2$H$_4$)$_3$ | 90 | 8 | =Z$_n$ | 3 | 6 | 7.0 | 1.0 | 138 | 16.5 | 1.4703 |
| q | n-C$_3$H$_7$ | C$_2$H$_5$ | 1.1 | 30 | C$_{18}$H$_{37}$ | 85 | 12 | 0.04 So | 1 | 4 | 4.3 | 3.0 | 63 | 13.7 | 1.4570 |
| r | n-C$_3$H$_7$ | C$_2$H$_5$ | 1.1 | 30 | C$_{18}$H$_{37}$ | 95 | 20 | 0.08 So | 1 | 8 | 8.7 | 7.0 | 36 | 16.0 | 1.4604 |
| s | C$_2$H$_5$ | CH$_2$—CHBr—CH$_2$Br | 1.2 | 15 | CH$_2$—CH—CH$_2$ | 85 | 7 | 0.1 So | 3 | 13.5 | 17.2 | 3.5 | 133 | 10.5 | 1.5068 |

EXAMPLE 7

Type of anhydride:

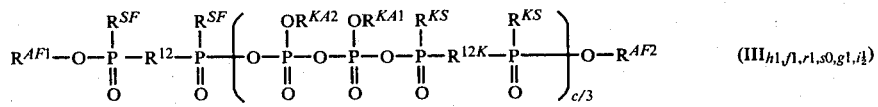 (III$_{h1,f1,r1,s0,g1,i1}$)

| R$^{12}$=R$^{12K}$ | R$^{AF1}$=R$^{KA1}$=R$^{SF}$=R$^{KA2}$=R$^{AF2}$=R$^{KS}$ | EP–MR | c | Z$_n$ | T | Zt | Kat | n | AA | AO (EO) | m | OHZ | P | n$_D$ |
|---|---|---|---|---|---|---|---|---|---|---|---|---|---|---|
| C$_2$H$_4$ | i-C$_4$H$_9$ | 1.2 | 15 | n-C$_6$H$_{12}$ | 110 | 9 | 0.03 So | 2 | 5 | 8 | 1.5 | 118 | 18.8 | |

EXAMPLE 8

Type of anhydride:

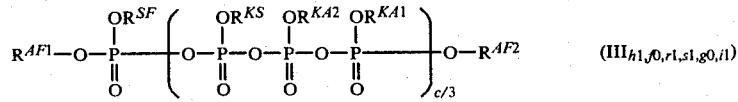 (III$_{h1,f0,r1,s1,g0,i1}$)

| | R$^{AF1}$=R$^{SF}$=R$^{AF2}$ R$^{KA1}$=R$^{KS}$=R$^{KA2}$ | EP–MR | c | Z$_n$ | T | Zt | Kat | n | AA | AO (EO) | m | OHZ | P | n$_D$ |
|---|---|---|---|---|---|---|---|---|---|---|---|---|---|---|
| a | CH$_3$ | 1.1 | 30 | C$-$(CH$_2$)$_4$ | 120 | 6 | — | 4 | 4 | 6.9 | 0 | 266 | 5.0 | 4.4619 |
| b | C$_2$H$_5$ | 2.0 | 3 | n-C$_6$H$_{12}$ | 85 | 3 | 0.03 So | 2 | 2 | 2.9 | 0 | 174 | 14.2 | 1.4445 |
| c | C$_2$H$_5$ | 1.2 | 15 | C$-$(CH$_2$)$_4$ | 100 | 3 | 0.08 So | 4 | 8 | 9.9 | 1.0 | 153 | 17.1 | 1.4521 |
| d | C$_2$H$_5$ | 2.0 | 3 | C$-$(CH$_2$)$_4$ | 90 | 5 | 0.05 So | 4 | 4 | 5.2 | 0 | 211 | 16.0 | 1.4452 |
| e | C$_2$H$_5$ | 2.0 | 3 | C$-$(CH$_2$)$_4$ | 90 | 5 | 0.1 So | 4 | 8 | 8.6 | 1.0 | 109 | 17.8 | 1.4342 |
| f | C$_2$H$_5$ | 2.0 | 3 | C$-$(CH$_2$)$_4$ | 85 | 4 | 0.2 So | 4 | 16 | 16.1 | 3.0 | 85 | 19.0 | 1.4365 |
| g | C$_2$H$_5$ | 1.2 | 15 | C$-$(CH$_3$)$_2$ | 85 | 5 | 0.06 So | 2 | 6 | 6.8 | 2.0 | 111 | 17.6 | 1.4471 |
| h | C$_2$H$_5$ | 1.1 | 30 | C$-$(CH$_2$)$_4$ oxethyl- | 90 140N | 4 4N | 0.08 So | 4 | 8 | 9.2 | 1.0 | 184 | 18.6 | 1.4559 |

EXAMPLE 8-continued

Type of anhydride:

$$R^{AF1}-O-\underset{\underset{O}{\overset{\overset{OR^{SF}}{|}}{\overset{\|}{P}}}}{}-\left(O-\underset{\underset{O}{\overset{\overset{OR^{KS}}{|}}{\overset{\|}{P}}}}{}-O-\underset{\underset{O}{\overset{\overset{OR^{KA2}}{|}}{\overset{\|}{P}}}}{}-O-\underset{\underset{O}{\overset{\overset{OR^{KA1}}{|}}{\overset{\|}{P}}}}{}\right)_{c/3}-O-R^{AF2} \qquad (III_{h1,f0,r1,s1,g0,i1})$$

| | $R^{AF1}=R^{SF}=R^{AF2}$ $R^{KA1}=R^{KS}=R^{KA2}$ | EP—MR | c | $Z_n$ | T | Zt | Kat | n | AA | AO (EO) | m | OHZ | P | $n_D$ |
|---|---|---|---|---|---|---|---|---|---|---|---|---|---|---|
| i | $C_2H_5$ | 1.1 | 30 | eneated glycerol (molecular weight 220) | 80 140N | 4 1N | 0.06 So | 3 | 6 | 7.8 | 1.0 | 147 | 15.2 | 1.4596 |
| j | $C_2H_5$ | 1.1 | 30 | oxethyl- eneated glycerol (molecular weight 220) | 85 140N | 11 1N | 0.12 So | 3 | 12 | 14.0 | 3.0 | 76 | 17.1 | 1.4579 |
| k | $C_2H_5$ | 1.1 | 30 | 3 O$-(C_2H_4)_2+$ 1 N$-(C_2H_4)_3$ | 80 | 7 | $=Z_n$ | 9 | 15 | 19.0 | 0.4 | 180 | 16.0 | 1.4559 |
| l | $CH_3$ | 1.1 | 30 | $n-C_6H_{12}$ | 120 | 8 | 0.02 So | 2 | 4 | 4.5 | 1.0 | 141 | 18.0 | 1.4597 |

EXAMPLE 9

Type of anhydride:

$$R^{AF1}-O-\underset{\underset{O}{\overset{\overset{OR^{SF}}{|}}{\overset{\|}{P}}}}{}-R^{12}-\underset{\underset{O}{\overset{\overset{OR^{SF}}{|}}{\overset{\|}{P}}}}{}-\left(O-\underset{\underset{O}{\overset{\overset{OR^{KA1}}{|}}{\overset{\|}{P}}}}{}-O-\underset{\underset{O}{\overset{\overset{OR^{KA2}}{|}}{\overset{\|}{P}}}}{}-O-\underset{\underset{O}{\overset{\overset{O-R^{KS}}{|}}{\overset{\|}{P}}}}{}-R^{12}-\underset{\underset{O}{\overset{\overset{O-R^{KS}}{|}}{\overset{\|}{P}}}}{}\right)_{c/3}-O-R^{AF2} \qquad (III_{h1,f1,r1,s1,g\frac{1}{2},i1})$$

| $R^{12}$ $=R^{12K}$ | $R^{AF1}$ $=R^{KA1}$ | $R^{SF}=R^{AF2}$ $=R^{KS}=R^{KA2}$ | EP—MR | c | $Z_n$ | T | Zt | Kat | n | AA | AO (EO) | m | OHZ | P | $n_D$ |
|---|---|---|---|---|---|---|---|---|---|---|---|---|---|---|---|
| $CH_2$ | $C_2H_5$ | $C_2H_5$ | 2.0 | 3 | $C-(CH_2)_4$ | 90 | 9 | 0.05 So | 4 | 4 | 9.4 | 0 | 198 | 21.5 | 1.4626 |

EXAMPLE 10

Type of anhydride:

$$HO-\underset{\underset{O}{\overset{\overset{R^{SF}}{|}}{\overset{\|}{P}}}}{}-\left(O-\underset{\underset{O}{\overset{\overset{R^{K}}{|}}{\overset{\|}{P}}}}{}\right)_{c}-O-H \qquad (III_{2H,h1,f0,r1,s0,g0,i0})$$

| | $R^{SF}$ $=R^{K}$ | KS—MR=c | $Z_n$ | T | Zt | Kat | n | AH | AA | AO | m | OHZ | P | $n_D$ |
|---|---|---|---|---|---|---|---|---|---|---|---|---|---|---|
| a | $C_3H_7$ | 5.0 | — | 140 150N | 10 1N | 0.04 So 0.03 SoN | — | 2 | 5.0 | 7.1 | 1.5 | 81 | 19.5 | 1.4701 |
| b | $C_3H_7$ | 20.0 | $CH_2-CH-CH_2$ | 135 30N | 8 1N | 0.04 So 0.1 NaMLN | 3 | 0.9 | 9.0 | 11.2 | 2.2 | 167 | 17.5 | 1.4720 |

EXAMPLE 11

Type of anhydride:

$$HO-\underset{\underset{O}{\overset{\overset{R^{SF}}{|}}{\overset{\|}{P}}}}{}-R^{12}-\underset{\underset{O}{\overset{\overset{R^{SF}}{|}}{\overset{\|}{P}}}}{}-\left(O-\underset{\underset{O}{\overset{\overset{R^{K}}{|}}{\overset{\|}{P}}}}{}\right)_{c}-O-H \qquad (III_{H2,f1,r1,s0,g0,i0})$$

| $R^{12}$ | $R^{SF}$ | KS—MR= =c=AA | T | Zt | Kat | AH | AO (EO) | m | OHZ | P |
|---|---|---|---|---|---|---|---|---|---|---|
| $C_2H_5$ | $CH_3$ | 10 | 185 | 24 | 0.1 So | 2 | 15.0 | 4.0 | 40 | 19.7 |

EXAMPLE 12

Type of anhydride:

$$HO-\underset{\underset{O}{\overset{\overset{R^{SF}}{|}}{\overset{\|}{P}}}}{}-\left(O-\underset{\underset{O}{\overset{\overset{R^{K}}{|}}{\overset{\|}{P}}}}{}-R^{12K}-\underset{\underset{O}{\overset{\overset{R^{K}}{|}}{\overset{\|}{P}}}}{}\right)_{c}-O-H \qquad (III_{H2,h1,f0,r1,s0,g1,i0})$$

| $R^{SF}$ | $R^{K}$ | $R^{K12}$ | KS—MR= =c=AA | T | Zt | Kat | AH | AO (EO) | m | OHZ | P | $n_d$ |
|---|---|---|---|---|---|---|---|---|---|---|---|---|
| $C_3H_7$ | $CH_3$ | $C_{10}H_{20}$ | 10.0 | 140 | 4 | 0.5 NaM | 2 | 15.7 | 4.0 | 49 | 18.3 | 1.4930 |

EXAMPLE 13

Type of anhydride:

$$HO-\underset{\underset{O}{\|}}{\overset{\overset{R^{SF}}{|}}{P}}-R^{12}-\underset{\underset{O}{\|}}{\overset{\overset{R^{SF}}{|}}{P}}\left(-O-\underset{\underset{O}{\|}}{\overset{\overset{R^{K}}{|}}{P}}-R^{12K}-\underset{\underset{O}{\|}}{\overset{\overset{R^{K}}{|}}{P}}-\right)_{c}O-H \quad (III_{2H,h1,f1,r1,s0,g1,i0})$$

| $R^{SF}$ | $R^{12}=R^{12K}$ | $R^K$ | KS−MR=c=AA | T | Zt | Kat | AH | AO (EO) | m | OHZ | P | $n_D$ |
|---|---|---|---|---|---|---|---|---|---|---|---|---|
| $CH_3$ | $C_2H_4$ | $CH_3$ | 100 | 150 | 16 | — | 2 | 107 | 49 | 50 | 28,8 | too viscous |

EXAMPLE 14

Type of anhydride:

$$HO-\underset{\underset{O}{\|}}{\overset{\overset{HO}{|}}{P}}-R^{12}-\underset{\underset{O}{\|}}{\overset{\overset{OH}{|}}{P}}\left(-O-\underset{\underset{O}{\|}}{\overset{\overset{R^K}{|}}{P}}-\right)_{cK}\left(-O-\underset{\underset{O}{\|}}{\overset{\overset{OH}{|}}{P}}-R^{12}-\underset{\underset{O}{\|}}{\overset{\overset{OH}{|}}{P}}-\right)_{cA=1}O-H \quad (III_{AN,6H,h1,f1,r1,s1,g0,i0})$$

| $R^{12}$ | $R^K$ | KAN−MR=$c^K$ | c=$c^K$+1 =AA | T | Zt | Kat | AH | AO (EO) | m | OHZ | P | $n_D$ |
|---|---|---|---|---|---|---|---|---|---|---|---|---|
| $C_4H_8$ | $C_2H_5$ | 18.0 | 19 | 150 | 7 | 0.05 | 6 | 27.2 | 2.2 | 121 | 18.9 | 1.4820 |

EXAMPLE 15

Type of anhydride

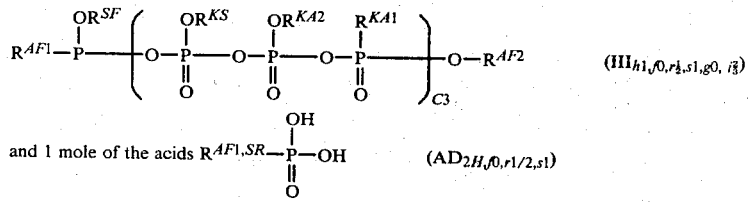

(III$_{AN,h1,f0,r0,s0,g1,i0}$)

| $R^{AF1}$=$R^{AF2}$ | $R^{SF}$ | $R^K$ | $R^{K12}$ | KAN−MR=$c^K$ | c=$c^K$+1 | $Z_n$ | T | Zt | Kat | n | AA | AO (EO) | m | OHZ | P | $n_D$ |
|---|---|---|---|---|---|---|---|---|---|---|---|---|---|---|---|---|
| $P_2H_5$ | $CH_3$ | $CH_3$ | $C_{10}H_{20}$ | 5 | 6 | C$(CH_2)_4$Po | 140 | 4 | 0.04 | 4 | 12 | 13.4 | 2.0 | 79 | 18.9 | 1.4926 |

EXAMPLE 16

Type of anhydride:

Proton-containing anhydride mixture consisting of $\frac{KS-MR}{c}$ moles of the terminated proton-free anhydrides $$R^{AF1}-\underset{\underset{O}{\|}}{\overset{\overset{OR^{SF}}{|}}{P}}\left(-O-\underset{\underset{O}{\|}}{\overset{\overset{OR^{KS}}{|}}{P}}-O-\underset{\underset{O}{\|}}{\overset{\overset{OR^{KA2}}{|}}{P}}-O-\underset{\underset{O}{\|}}{\overset{\overset{R^{KA1}}{|}}{P}}-\right)_{c3}O-R^{AF2} \quad (III_{h1,f0,r\frac{1}{2},s1,g0,i\frac{3}{2}})$$

and 1 mole of the acids $R^{AF1,SR}-\underset{\underset{O}{\|}}{\overset{\overset{OH}{|}}{P}}-OH$   (AD$_{2H,f0,r1/2,s1}$)

as proton-containing outer group donors (AD$_H$).

| $R^{AF1}$=$R^{KA1}$ | $R^{SF}$=$R^{KS}$=$R^{AF2}$=$R^{KA2}$ | $R^{AF1,SR}$ | EP−MR | c | KS−MR=AA | T | Zt | Kat | AH | AO (EO) | m | OHZ | P | $n_D$ |
|---|---|---|---|---|---|---|---|---|---|---|---|---|---|---|
| a n-$C_3H_7$ | n-$C_2H_5$ | $C_3H_7$ | 1.1 | 30 | 4.0 | 95 | 7 | 0.04So | 2 | 6.3 | 1.0 | 105 | 18.2 | 1.4790 |
| b n-$C_3H_7$ | $CH_3$ | n-$C_8H_{17}$ | 1.1 | 30 | 4.0 | 125 | 8 | 0.15NaM | 2 | 6.3 | 1.0 | 100 | 17.8 | 1.4665 |
| c CN−$C_2H_4$ | $C_2H_5$ | n-$C_3H_7$ | 1.2 | 15 | 5.0 | 90 30N | 9 1N | 0.01So 0.1NaMIN$^2$ |  | 8.5 | 1.5 | 101 | 17.3 | 1.4732 |

EXAMPLE 17

Type of anhydride:

Proton-containing anhydride mixture consisting of $\frac{KS-MR}{c}$ moles of the terminated proton-free anhydrides as in Example 16 and 1 mole of

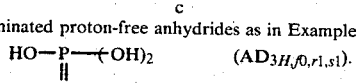   (AD$_{3H,f0,r1,s1}$).

| $R^{AF1}$=$R^{KA1}$ | $R^{SF}$=$R^{KS}$=$R^{AF2}$=$R^{KA2}$ | EP−MR | c | KS−MR=AA | T | Zt | Kat | AH | AO (EO) | m | OHZ | P | $n_D$ |
|---|---|---|---|---|---|---|---|---|---|---|---|---|---|
| n-$C_3H_7$ | $C_2H_5$ | 1.1 | 30 | 6 | 110 | 9 | 0.1 NaM | 3 | 10.3 | 1.0 | 132 | 18.0 | 1.4626 |

EXAMPLE 18

Type of anhydride:

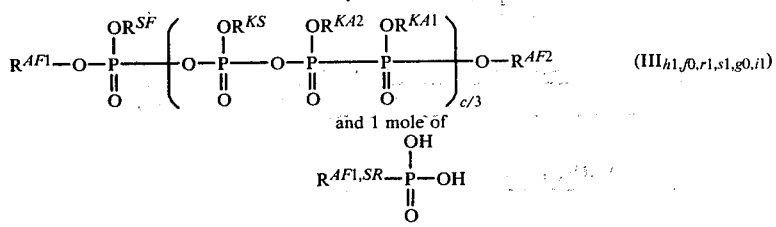

Proton-containing anhydride mixture consisting of $$\frac{MS-MR}{c}$$

moles of a terminated proton-free anhydride of the type $(III_{h1,f0,r1,s1,g0,i1})$ and 1 mole of $$R^{AF1,SR}-\underset{\underset{O}{\|}}{P}-OH$$
$$\phantom{R^{AF1,SR}-P}|\phantom{-OH}$$
$$\phantom{R^{AF1,SR}-P}OH$$

| $R^{AF1}=R^{SF}=A^{AF2}$<br>$=R^{KS}=R^{KA2}=R^{KA1}$ | $R^{AF1,SR}$ | EP—MR | c | KS—MR=AA | T | Zt | Kat | AH | AO | m | OHZ | P | $n_D^{20}$ |
|---|---|---|---|---|---|---|---|---|---|---|---|---|---|
| CH$_3$ | C$_3$H$_7$ | 1.1 | 30 | 5.0 | 140 | 5 | 0.01 So | 2 | 8.3 | 1.5 | | 19.4 | 1.4606 |

EXAMPLE 19

Types of anhydride: PL = 2,5-di-oxo-2-methyl-1,2-oxa-phospholane and also
EBA = 1,2-ethane-bis-(methyl-phosphinic acid) anhydride
PPA = propanephosphonic acid anhydride
TPPO = adduct of 1 mole of P$_2$O$_5$ and 1.2 moles of triethyl phosphate Furthermore, in this example: PHSR = phosphorus-containing acid
PPS = propanephosphonic acid and
PRS = phosphoric acid

| | $Z_n$ | n | PHSR | AH | T | Zt | Kat | AA$_{PL}$ | AA$_{EBA}$ | AA$_{PPA}$ | AA$_{TPPO}$ | AA | AO | m | OHZ | P | $n_D$ |
|---|---|---|---|---|---|---|---|---|---|---|---|---|---|---|---|---|---|
| a | C$_4$H$_8$ | 2 | — | — | 135 | 5 | 0.01So | 2 | 1 | 1 | — | 4 | 4.1 | 1.0 | | 19.0 | 1.4924 |
| b | — | — | PPS | 2 | 130 | 7 | 0.02So | 5 | — | 5 | — | 10 | 12.4 | 4.0 | | 18.2 | 1.4869 |
| c | — | — | PRS | 3 | 145 | 11 | 0.04So | 2 | — | — | 4 | 6 | 9.8 | 1.0 | 139 | 18.4 | 1.4706 |

EXAMPLE 20: multi-stage process (MSP)

(a) Anhydride characteristic: III$_{hO,gO,iO}$

1st Stage SR: 212 g (2 moles) of propanephosphonic acid anhydride are heated to 80° C., 118.1 g (1 mole) of 1,6-hexane-diol are introduced in the course of 20 minutes, with cooling, and the mixture is stirred for a further 30 minutes at 80° C. 330 g of a syrup with an acid number of 317, a phosphorus content of 18.8% and a $n_D^{20}=1.4683$ result.

2nd Stage m=O: 100 g (2.27 moles) of ethylene oxide are passed in in the course of 5 hours, at 145° C., and 430 g of an oil for which SZ=1, $n_D^{20}=1.4669$ and OHZ=270 and which has a phosphorus content of 14.4% are obtained.

3rd Stage m=O, q=1: After adding 212 g (2 moles) of further propanephosphonic acid anhydride at 80° C., 641 g of a syrup with an acid number of 165 and a $n_D^{20}=1.4709$ and a phosphorus content of 19.3% result.

4th Stage m=1, q=O: A further 88 g (2.0 moles) of ethylene oxide are passed in at 90° C. 728 g of an oil with an acid number of 2, a OHZ of 158, P=17.0% and $n_D^{20}=1.4694$ form.

(b) Anhydride characteristic: III$_{hO,gl,iO}$

1st Stage SR: 90.1 g (1 mole) of 1,4-butanediol and 1 g of sodium carbonate are added to 448 g (2 moles) of 1,6-hexane-bis-(methyl-phosphinic acid) anhydride in the course of 10 minutes, at 110° C. The temperature rises to 120° C. 539 g of product having an acid number of 206 result.

2nd Stage m=O: 110 g (2.5 moles) of ethylene oxide are introduced in the course of 4 hours at 130° C. 648 g of a viscous syrup with an acid number of 0.8, a OHZ of 180, P=19.1% and $n_D^{20}=1.4970$ result.

3rd Stage m=O and q—1: A further 448 g (2 moles) of 1,6-hexane-bis(methyl-phosphinic acid) anhydride are added at 120° C. and the mixture is stirred for a further 30 minutes. 1,096 g of a bis-functional viscous acid result. Acid number=102, P=22.96% and $n_D^{20}=1.5042$.

4th Stage m=1 and q=O: A further 89 g (2.02 moles) of ethylene oxide are passed in in the course of 8 hours, at 135° C., and 1.184 g of a highly viscous pale yellow syrup with an acid number of 2, a OHZ of 99, P=20.9% and $n_D^{20}=1.5013$ are obtained.

The phosphorus-containing polyadducts according to the invention, which are distinguished by a very good solubility in water or by the fact that they are readily emulsifiable and which possess a high phosphorus content, can be fixed to textile material by means of very diverse reactive crosslinking agents. The finishes thus obtained display very good flame-retardant and permanent properties.

Crosslinking agents which can be used are polyfunctional N-methylol compounds, for example derivatives of amino-1,3,5-triazines, such as trimethylolmelamine, hexamethylolmelamine, trimethylolmelamine trimethyl ether, hexamethylolmelamine pentamethyl ether, trimethylolmelamine triisobutyl ether and dimethylol-acetoguanamine, and also derivatives of ureas, such as dimethylolurea, dimethylolurea dimethyl ether, dimethylolurea dibutyl ether, dimethylolcycloethyleneurea, dimethylolcyclopropyleneurea, dimethylol-4-methoxy-5-dimethyl-propyleneurea, dimethylol-5-hydroxypropyleneurea, 1,3-dimethylol-4,5-dihydroxyimidazolidone-(2), 1,3-dimethylol-5-hydroxyethylhexahydrotriazine-(2), dimethylolurone and dimethylolcarbamates, such as, for example, methyl dimethylolcarbamate, hydroxyethyl dimethylolcarbamate and methoxyethyl dimethylolcabamate.

Interesting compounds, which have proved particularly suitable, are the melamine derivatives, for example trimethylolmelamine trimethyl ether or hexamethylolmelamine pentamethyl ether.

The catalysts added, which show their action in an acid pH range, are, in general, about 0.2 to 5 percent by weight, preferably 0.4 to 3 percent by weight, of inorganic or organic acids, or their salts which liberate the acid by hydrolysis or by a heat treatment, such as, for example, sulfuric acid, hydrochloric acid, phosphoric acid, trichloroacetic acid, maleic acid, tartaric acid, citric acid, acetic acid or their salts with ammonia, amines or polyvalalent metals, preferably salts of strong or medium strength acids, such as ammonium sulfate, ammonium chloride, mono- and di-ammonium oxalate, ammonium nitrate, magnesium chloride, aluminum chloride, zinc chloride, zinc nitrate, zinc fluoborate and 2-amino-2-methylpropanol hydrochloride.

The crosslinking catalysts can be employed on their own or as mixtures with one another.

The textile material on which it is possible to provide the flame-retardant and permanent finishes can be very diverse. Excellent flameproofing effects are achieved on cellulose fiber fabrics, polyester and polyamide fabrics and plastic-bonded or plastic-reinforced glass fiber fabrics and on textile wall coverings or textile blinds made of cellulose fibers, polyester or polyamide fibers, glass fibers or mixtures thereof. Fabrics suitable as synthetic or mixed fiber material are, in particular, nonwoven fabrics, for example needle-punched felts for wall and floor coverings, textile wall coverings, insulating materials and air filters of very diverse composition, such as, for example, needle-punched felts made of 50/50 polyester/polyamide 6 fibers, 100% pure polyamide fibers, 100% pure polyester fibers, 50/50 polyamide fibers and viscose staple, 50/50 or 75/25 polyester fibers with viscose staple, 50/25/25 polyamide/polyacrylonitrile and polyester fibers, 75/25 glass fibers with polyester fibers, 50/50 wool/polyamide fibers and 100% pure polypropylene fibers or mixtures thereof with other synthetic or natural or regenerated cellulose fibers.

The process according to the invention for providing the textile materials described above with a flame-retardant finish is carried out under application conditions which are known and customary in the textile industry. An additional operation which changes the sequence of operations for finishing the said textile material is not necessary. The fabrics or needle-punched felts are treated with the aqueous finishing liquors on a two-roll or three-roll padder, squeezed off and subjected to a drying process and a curing process.

When providing cellulose, polyester or polyamide fiber fabrics, glass fiber fabrics, textile wall coverings or textile blinds with a flame-retardant finish, the heat treatment preferably takes place in two stages. The fabrics are first dried above about 50° C., preferably at about 100° to 120° C. in order to remove the water down to a residual value of about 4–8% and curing is then allowed to take place at about 140° to 180° C. for about 7 to 3 minutes.

Needle-punched felt carpeting can also be provided with a flame-retardant finish by the two-stage process. In this case, however, the crosslinking preferably takes place in a single-stage drying and curing process at about 120° to about 180° C. and in the main at 135° to 160° C. The heat treatment takes on average about 7 to about 60, preferably 10 to 30, minutes. The heat treatment is carried out in drying chambers or on stenter frames, hot flues or curing frames.

Further finishing agents, such as textile softeners, products imparting hydrophobic properties, products imparting oleophobic properties or also products providing an antimicrobial finish, can be added to the finishing liquors.

The very good flame-retardant effects of the phosphorus-organic compounds claimed enable application to be made to pile carpets—woven or tufted carpets—via the back of the carpet or via the pre-coat. As is known, finishing on the back of the carpet is responsible for the dimensional stability of woven carpets and the pre-coat is responsible for binding the pile filaments in the tufting backing.

As a result of these measures, that is to say the anchoring of the phosphorus-organic compounds in the finish on the back of the carpet or in the pre-coat, full bath impregnation is superfluous. In full bath impregnation, the pile filaments are also brought into contact with the flameproofing agents, crosslinking agents, catalysts and binders based on polymer dispersions. As a result of this type of treatment of the carpet pile, the flameproofing agents and the other finishing products in the impregnating liquor then lie on or between the pile filaments and lead to sticking. The individual filaments of the pile should, on the contrary, remain movable. Moreover, sticking of the pile can result in more extensive soiling. The flameproofing products can also gradually be removed when the carpets are walked on.

The finishes obtained in this way on pile carpets are also distinguished by their very good flame-retardant properties, for example on treatment with shampoos and when the carpets are washed.

The backing of the tufted carpets can consist of cotton, jute, rayon staple, wool or synthetic fibers based on polyamide or polyester or polypropylene or a mixture of these, or of glass fibers. Needle-punched non-wovens of polyester or polypropylene fibers are also outstandingly suitable as backings for the process according to the invention.

Material which can be used as pile filaments for tufted carpets and for woven carpets is fiber material of wool, polyamide or polyester and also polyacrylonitrile, or mixtures thereof, for example 80/20 polyacrylonitrile/polyester. Fiber material of wool, polyamide or polyester filaments having the customary cut height of 4–12 mm is preferred.

Commercially available 40–50% strength polymer dispersions are employed to impart the desired handle to cellulose fiber fabrics, polyester and polyamide fabrics, glass fiber fabrics, textile wall coverings or textile blinds, to improve the resistance to rubbing and the firmness under foot of the needle-punched felt carpeting, to strengthen nonwovens, for binding the pile filaments in tufted goods into the backing by the so-called pre-coat or for finishing woven carpets on the back.

Polymer dispersions which can be used are polyvinyl acetate, polyvinyl acetate with plasticizers for polymers, such as dibutyl phthalate, copolymers of vinyl acetate and dibutyl maleate, copolymers of butyl acrylate and N-methylolacrylamide, copolymers of butyl acrylate, N-methylolacrylamide and acrylic acid, copolymers of butyl acrylate, N-methylolacrylamide and/or N-methylolmethacrylamide and acrylic acid, copolymers of butyl acrylate, methyl methacrylate and methylolmethacrylamide, copolymers of butyl acrylate, acrylonitrile, N-methylolacrylamide and methacrylic acid, copolymers of butyl acrylate, ethyl acrylate, acrylonitrile, N-methylolmethacrylamide and acrylic acid, copolymers of butyl acrylate, styrene, acrylonitrile and N-methylolmethacrylamide, copolymers of N-methylolmethacrylamide and butanediol diacrylate, methyl acrylate and butyl acrylate, copolymers of ethyl acrylate, acrylonitrile and N-methylolacrylamide, copolymers of butyl acrylate, vinyl acetate and N-methylolacrylamide, copolymers of butyl acrylate, acrylonitrile and N-methylolacrylamide, copolymers of styrene, butyl acrylate and acrylic acid, natural latex or synthetic latices of styrene and butadiene.

Preferred polymer dispersions are polyvinyl acetate dispersions (50% strength), copolymers of vinyl acetate and dibutyl maleate, for example in a ratio of 77/23 (about 50% strength), copolymers of styrene/butyl acrylate/acrylonitrile/methacrylic acid/acrylamide, for example in a ratio of 16:61:25:2:1 or 25:53:25:1, copolymers of ethyl acrylate/acrylonitrile/N-methylolacrylamide, 6:3:1, copolymers of butyl acrylate/vinyl acetate/N-methylolacrylamide, 35:55:10, and also graft polymers (partially saponified), such as 50% polyvinyl alcohol, 25% polyvinyl acetate and 25% polyethylene, or butadiene/styrene latex (about 50%), for example in a ratio of 40:60, 60:40 or 35:60+3.5 acrylic acid.

The impregnating liquors, both for the pre-coat and for the back coating in the case of woven carpets, also contain thickeners which are intended to prevent the finishing solution penetrating into the pile and causing this to stick. Suitable thickeners are water-soluble hydroxyethylcelluloses, methylcelluloses and carboxymethylcelluloses, water-soluble starch products, partially etherified or etherified starch products, polyvinyl alcohols and the Na or ammonium salts of alginic acid.

The pre-coat or the coating on the back of the carpet in the case of woven carpets can also be filled with chalk in the conventional manner. However, metal oxides, such as, for example, aluminum oxide, aluminum hydroxide or hydrated aluminum oxide, can also be used as fillers.

The process according to the invention for providing a flame-retardant finish on pile carpets or on woven carpets by coating on the back is also carried out under application conditions which are customary in the textile industry.

The pre-coat composition, for tufted carpets, or the back finish, for woven carpets, which contains the flame-retardant compound, the cross-linking agent, the polymer dispersion and the catalyst is applied with the aid of an air knife, a rubber sheet doctor or a doctor roller. Drying and curing are then carried out on a stenter frame, in gelling or drying tunnels or cylinder dryers at 125° to 150° C. The residence time depends on the thickness of the carpets and is between 5 and 20 minutes and in the main 7 to 10 minutes.

In the case of tufted carpets, this procedure is generally followed by coating on the back with natural latex or a synthetic latex dispersion, for example based on butadiene/styrene, 40:60 or 60:40.

When tufted goods which have been provided, according to the invention, with a flame-retardant finish via the pre-coat and which also carry a latex coating on the back are tested to determine the burning or combustion characteristics, excellent flameproofing for the entire carpet is found. The flameproofed pre-coat forms a barrier layer against the latex back, so that the latter does not ignite.

The flameproofing process according to the invention is also distinguished by the fact that no aggressive vapors, in the form of a hydrogen halide, can form when a flame acts on the goods; when flame-retardant component products based on chlorinated paraffins, PVC or inorganic or organic bromine compounds are employed, such vapors form to a substantial degree.

The flame-retardant systems described are distinguished, on the various textile materials, by very good permanence. The flame-retardant finishes have an elastic handle and when subjected to mechanical stress, for example rolling up of needle-punched felt carpeting, tufted carpets or woven carpets, or bending sharply, do not result in breaking or powdering of the finish. These elastic properties of the finishes, which also display no or only very slight swelling when subjected to wet treatments, are probably partly responsible for the very good permanency to washing, on the textile materials described, and for the excellent binding of the pile filaments in the tufting backing.

The finishes in general also display good anti-static properties and in many cases render the addition of anti-static agents or carbon black dispersions superfluous. The incorporation of anti-static products, textile softeners or agents imparting oleophobic properties in general does not present any difficulties.

USE EXAMPLES

Example 1

Coarse-filament needle-punched felt carpeting which consists of a polyester fiber core and a polyamide outer surface in a mixing ratio of 65:35 and has a weight per square meter of about 800 g/m² is treated on a two-roller padder with an aqueous solution which consists of the following individual components: 330 g/l of a reaction product of 8 moles of propanephosphonic acid anhydride, 1 mole of pentaerythritol and 9.3 moles of ethylene oxide (Example 1–0), 160 g/l of trimethylolmelamine trimethyl ether (80% strength), 5 g/l of zinc chloride and 200 g/l of a 40% strength polymer dispersion of ethyl acrylate/acrylonitrile/N-methylolacrylamide in a ratio of 6:3:1. The squeeze-off effect is about 105%. The goods are then dried for 20 minutes at 145° C.

The needle-punched felt displays a very good flame-proofing effect, which survives several shampooings and low-temperature washes at 40°–50° C. The flame-proofing test is carried out in accordance with DIN 54,333, which relates to the determination of the speed of flame propagation in textiles, or in accordance with the vehicle safety standard No. 302 (US-MVSS 302).

The needle-punched felt carpeting finished according to the invention does not continue to burn after the test flame has been removed. Outside the test length, only aftersmouldering for 10–15 seconds was discernible. The needle-punched felt also does not continue to burn after it has been subjected to three low-temperature washes with 2 g/l of a commercially available washing agent for delicate fabrics (the washing time is 15 minutes at 40° C. in each case). The time for which the flame continues to burn had increased only to 40–60 seconds. The needle-punched felt also does not continue to burn after it has been shampooed 5 times. The time for which the flame continues to burn is 50 seconds.

If, on the other hand, the needle-punched felt carpeting is finished with 200 g/l of the polymer dispersion mentioned in the example, the needle-punched felt burns away on a broad front in 3 minutes and 45 seconds after the flame has been removed.

The needle-punched felt provided with a flame-retardant finish is elastic and dimensionally stable.

Example 2

The reaction product of propanephosphonic acid anhydride, pentaerythritol and ethylene oxide described in Example 1 is used as the flame-retardant component of a pre-coat finish for tufted goods.

The tufted goods (which have a weight per square meter of 650 g/m$^2$), which consist of a 6 mm high polyamide loop pile tufted on a support material of needle-punched polypropylene non-woven fabric, are finished with a pre-coat of the following composition: 330 parts of a reaction product of 8 moles of propanephosphonic acid anhydride, 1 mole of pentaerythritol and 9.3 moles of ethylene oxide (Example 1-0), 160 parts of trimethylolmelamine trimethyl ether (80% strength), 150 parts of a 50% strength butadiene/styrene dispersion (60:40), 300 parts of a 3.5% strength solution of methyl-hydroxyethylcellulose, 275 parts of water, 5 parts of ammonium chloride and 400 parts of chalk.

The pre-coat is applied with the aid of a rubber sheet doctor and dried for 10 minutes at 145° C. The application must be so regulated that the dry coating is about 800 g/m$^2$.

The treated tufted carpet has a flexible handle and excellent dimensional stability. The impregnating solution has not penetrated into the pile filaments. The polyamide pile displays its original mobility. The anchoring of the pile filaments in the backing is excellent.

After the above procedure, a coating on the back of the carpet is applied, by the foam process, on a rubber sheet doctor.

The coating liquor consists of 205 parts of a 50% strength butadiene/styrene dispersion (40/60), 14 parts of a paste containing vulcanizing accelerators, 300 parts of chalk and 8 parts of a foam based on a Na alkylnaphthalenesulfonate. Foaming is in a ratio of 1:3 to the original volume. After application with the doctor, the coating is dried at 150° C. for 10 minutes. A smooth foam backing consisting of a dry coating of about 900 g/m$^2$ forms.

Parallel to the above, a cut piece of the tufted goods described above is provided with a pre-coat which does not contain a flame-retardant component. The pile filaments are bound with a 50% strength butadiene/styrene dispersion (60:40), chalk and methyl-hydroxyethylcellulose as the thickener. After drying, the smooth foam described above is then applied. Flameproofing test:

The cut pieces of carpet, that is to say that provided with a flame-retardant finish via the pre-coat and that which has not been provided with a flame-retardant finish, are tested in accordance with DIN Standard 54,332 after a flame has been applied for 15, 30 and 60 seconds. The following picture emerges:

The cut piece of carpet which has not been provided with a flame-retardant finish burns away, whilst the carpet provided with a flame-retardant finish does not continue to burn after the test flame has been removed.

The flameproofing test according to the Nordtest method No. 7 gives the following findings: The cut pieces of carpet which does not contain any flame-retardant pre-coat shows no flameproofing according to Nordtest method No. 7. After extinguishing of the pile of wood, the cut piece of carpet continues to burn on a broad front beyond the scale marking at 60 cm. The cut piece of carpet provided with a flame-retardant finish is extinguished after the pile of wood has burnt away and shows a burn length of 30 cm, a burn width of 12 cm and after-burning for 10 seconds. The smooth foam back provided with a flame-retardant finish is not affected by the action of the flame.

The excellent flame-retardant effect is retained even after 6 shampooings or after several wet treatments.

Example 3

The tufted carpet described in Example 2 is treated with a pre-coat impregnating liquor which has the following composition: 280 parts of a reaction product of 1 mole of glycerol, 9 moles of ethanephosphonic acid anhydride and 10.4 moles of ethylene oxide (Example 1g), 140 parts of trimethylolmelamine trimethyl ether (80% strength), 150 parts of a 50% strength butadiene/styrene dispersion (60:40), 400 parts of a 3.0% strength solution of methyl-hydroxyethylcellulose, 175 parts of water, 5 parts of ammonium chloride and 350 parts of chalk.

The pre-coat is again applied with the aid of a rubber sheet doctor and dried for 12 minutes at 140° C.

The dry coating is 780 g/m$^2$.

The tufted carpet finished in this way has an elastic handle. The carpet pile is not stuck since the pre-coat composition has not penetrated through the backing.

According to the flameproofing test by the Nordtest method No. 7 for floor coverings, the tufted carpet treated in this way does not continue to burn after the pile of wood has burnt away. The burn length is 30 cm and the burn width is 16 cm. After 3 minutes no further after-burning is observed.

The flame-retardant effect has an excellent stability to shampooing and survives several wet treatments.

Example 4

Needle-punched felt carpeting (700 g/m$^2$) which consists of a fine-filament polypropylene core and a coarse-filament outer face of polypropylene filaments is treated on a two-roll padder with an aqueous impregnating solution which has the following composition: 270 g/l of a reaction product of 1 mole of glycol, 10 moles of propanephosphonic acid anhydride and 11.2 moles of ethylene oxide (Example 1i), 140 g/l of trimethylolmelamine trimethyl ether (80% strength), 210 g/l of a 40% strength polymer dispersion of ethyl acrylate/acrylonitrile/N-methylolacrylamide (6:3:1) and 4.5 g/l of zinc chloride.

The squeeze-off effect is 110%. The goods are then dried for 25 minutes at 135° C.

The flame-retardant effect of the very elastic and dimensionally stable needle-punched felt is excellent and survives several shampoo treatments. The flame-retardant effect is tested in accordance with DIN 54,333 "Determination of the speed of flame propagation". After the test flame has been removed, the needle-punched felt continues to burn for 30 seconds outside the test zone. After shampooing 3 times, the needle-punched felt continues to burn for 60 seconds. The flame does not reach the test zone.

If, on the other hand, the needle-punched felt is finished only with 200 g/l of the polymer dispersion mentioned in the example, this needle-punched felt continues to burn after the test flame has been removed. The flame passes along 10 cm of the test distance in 2 minutes and 30 seconds.

Example 5

Excellent flame-retardant and permanent effects are obtained when the polypropylene needle-punched felt used in Example 4 is treated with the following aqueous finishing solution: 250 g/l of a reaction product of 1 mole of 1,4-butenediol, 12 moles of ethanephosphonic acid anhydride and 12.2 moles of ethylene oxide (Example 1h), 130 g/l of trimethylolmelamine trimethyl ether, 220 g/l of a 50% strength polymer dispersion of vinyl acetate and the dibutyl ester of melamine acid in a ratio of 77:23 and 25 g/l of a 40% strength solution of 2-amino-2-methyl-propanol hydrochloride. The squeeze-off effect is 95%. Drying is carried out for 25 minutes at 135° C.

Example 6

The tufted goods described in Example 2 are provided with a pre-coat which consists of the following individual components: 300 parts of a reaction product of 1 mole of 1,6-hexanediol, 8 moles of methanephosphonic acid anhydride and 9.1 moles of ethylene oxide (Example 1c), 140 parts of trimethylolmelamine trimethyl ether (80% strength), 150 parts of a 50% strength butadiene/styrene dispersion (60:40), 300 parts of a 3.0% strength solution of methyl-hydroxyethylcellulose, 275 parts of water, 5 parts of ammonium chloride and 400 parts of chalk.

The pre-coat is applied with the aid of a rubber sheet doctor and dried and cured for 15 minutes at 140° C. The dry coating is about 780 g/m$^2$.

The tufted carpet treated in this way has a flexible handle. The binding of the individual pile filaments in the backing is excellent. The finish applied does not break. The impregnating liquor has not penetrated into the pile filaments.

Parallel to the above, the same tufted goods are finished with the butadiene/styrene dispersion and the 3.0% strength solution of methylhydroxyethylcellulose only.

The great differences between the two finishes are shown in the combustion characteristics according to DIN Standard 54,333. Whilst the test piece of the tufted goods provided with a flame-retardant finish continues to burn for only 15 seconds after the test flame has been removed (the flame does not reach the test distance), the test piece without a flame-retardant finish continues to burn. The flame passes along a test distance of 10 cm in 2 minutes and 50 seconds.

Example 7

The needle-punched felt carpeting described in Example 4 is treated on a 2-roll padder with the following impregnating solution: 300 g/l of a reaction product of 1 mole of pentaerythritol, 8 moles of methanephosphonic acid anhydride and 9.1 moles of ethylene oxide (Example 1a), 140 g/l of trimethylolmelamine trimethyl ether (80% strength), 200 g/l of a 40% strength polymer dispersion of ethyl acrylate/acrylonitrile/N-methylolacrylamide in a ratio of 6:3:1 and 5 g/l of zinc chloride.

The squeeze-off effect is 95%. The goods are then dried for 20 minutes at 135° C.

The needle-punched felt displays a very good flame-proofing effect which survives several shampoo treatments and low-temperature washes at 40° C.

The flameproofing test is carried out in accordance with DIN 54,333.

The needle-punched felt test piece does not continue to burn after the test flame has been removed. Only afterburning for 10 seconds outside the test zone was discernible.

After subsequent washing three times with 2 g/l of a commercially available washing agent for delicate fabrics, the needle-punched felt likewise did not continue to burn after the test flame had been removed. The after-burning time is 55 seconds outside the test zone.

The needle-punched felt provided with a flame-retardant finish is elastic, lightly filled and dimensionally stable.

Example 8

The polypropylene needle-punched felt carpeting described in Examples 4 and 7 is treated with an impregnating liquor of the following composition: 290 g/l of a reaction product of 100 moles of propanephosphonic acid anhydride and 104 moles of ethylene oxide and 1 mole of sodium carbonate catalyst (Example 1k), 140 g/l of trimethylolmelamine trimethyl ether (80% strength), 220 g/l of a 40% strength polymer dispersion of ethyl acrylate/acrylonitrile/N-methylolacrylamide in a ratio of 6:3:1 and 5 g/l of ammonium chloride.

The squeeze-off effect is 105%. Drying and curing are then carried out for 25 minutes at 135° C.

The needle-punched felt has been provided with a very good permanent flame-retardant finish. The handle is elastic and lightly filled but not hardened.

Example 9

Tufted carpet goods having a weight per square meter of 650 g/m$^2$, which consist of a 6 mm high polyester pile, tufted on a support material of needle-punched polypropylene nonwoven fabric (100 g/m$^2$), are provided with a pre-coat of the following composition: 280 parts of a reaction product of 12 moles of propanephosphonic acid anhydride, 1 mole of pentaerythritol and 12.8 moles of ethylene oxide (Example 1m), 140 parts of trimethylolmelamine trimethyl ether (80% strength), 160 parts of a 50% strength butadiene/styrene dispersion (60:40), 300 parts of a 2.7% strength solution of methylhydroxyethylcellulose, 300 parts of water, 5 parts of ammonium chloride and 400 parts of chalk.

The pre-coat is applied with the aid of a hand doctor and dried for 10 minutes at 145° C. The dry coating is about 750 g/m$^2$.

The tufted carpet treated in this way has a flexible handle and very good dimensional stability. The pile filaments are very well anchored in the backing.

Following the above procedure, a coating on the back of the carpet is applied, as in Example 2, by the foam process using a rubber sheet doctor and the further processing is carried out as in Example 2. The tufted carpet treated in this way satisfies Test Standard DIN 54,333. After the test flame has been removed, the carpet continues to burn for only 20 seconds. The flame does not reach the test distance.

If the carpet is tested in accordance with DIN 54,332 (determination of the combustion characteristics of textile floor coverings), the flame being applied for 15, 30 and 60 seconds, the carpet does not continue to burn after the test flame has been removed. The foam backing which has not been provided with a flame-retardant finish is not affected. It is undamaged.

Example 10

Needle-punched felt carpeting of polypropylene fibers, as described in Example 4, is treated with an impregnating solution of the following composition: 220 g/l of a reaction product of 1 mole of pentaerythritol, 8 moles of 1,6-hexanebis-(methylphosphinic acid) anhydride and 10 moles of ethylene carbonate, which contains 21.0% of P (Example 4 g), 100 g/l of trimethylolmelamine trimethyl ether (80% strength), 200 g/l of a 40% strength polymer dispersion of ethyl acrylate/acrylonitrile/N-methylolacrylamide (6:3:1) and 4 g/l of ammonium chloride.

The needle-punched felt is treated on a 2-roll padder and squeezed off. 100% liquor pick-up.

The felt is then dried for 25 minutes at 135° C.

The needle-punched felt displays an excellent flameproofing effect according to U.S. Safety Standard for Vehicles No. 302 (US-MVSS 302). The needle-punched felt continued to burn for only 5 seconds after the test flame was removed.

The needle-punched felt is elastic and dimensionally stable.

Example 11

The needle-punched felt described in Example 1, which consists of a polyester fiber core and a polyamide outer face, is treated with an impregnating solution which has the following composition: 200 g/l of a reaction product of 1 mole of 1,6-hexanediol, 8 moles of methane-bis-methylphosphinic acid anhydride (Example 4 b) and 12 moles of ethylene oxide, which has a phosphorus content of 27.5% (Example 4 b), 150 g/l of trimethylolmelamine trimethyl ether (80% strength), 200 g/l of an approximately 45% strength styrene/butyl acrylate/acrylonitrile/methacrylic acid/acrylamide dispersion (ratio 16:61:25:2:1) and 20 g/l of a 40% strength solution of 2-amino-2-methylpropanol hydrochloride.

The needle-punched felt is squeezed off on a two-roll padder. Liquor pick-up 105%. Drying and curing are then carried out for 25 minutes at 140° C.

The needle-punched felt is lightly filled and elastic. The needle-punched felt also displays a very good flameproofing effect, which survives several shampoo treatments. The flameproofing test is carried out in accordance with DIN 54,333 "Determination of the speed of flame propagation in textiles". After the flame has been applied, the needle-punched felt continues to burn for 45 seconds, without reaching the test distance. After shampooing 3 times, the needle-punched felt continues to burn for 60 seconds after the test flame has been removed.

Example 12

The tufted carpet described in Example 2 is treated with the pre-coat impregnating solution indicated below, with the aid of a rubber sheet doctor: 220 parts of a reaction product of 1 mole of glycol, 4 moles of ethane-1,2-bis-(methylphosphinic acid anhydride) and 4.2 moles of ethylene oxide, which has a phosphorus content of 26.6% (Example 4d), 100 parts of an 80% strength trimethylolmelamine trimethyl ether solution, 300 parts of a 3.5% strength solution of methyl-hydroxyethylcellulose, 150 parts of a 50% strength butadiene/styrene dispersion (60:40), 5 parts of ammonium chloride and 225 parts of water.

After application by means of the doctor, the coating is dried for 20 minutes at 140° C.

The coating applied by means of the doctor is so regulated that the dry coating is about 750 g/m².

After drying, the tufted carpet provided with the precoat described above has a flexible handle and very good dimensional stability. The impregnating solution has not penetrated into the pile filaments.

The pile filaments have retained their full mobility and are not stuck on the walking surface side.

The tufted carpet finished in this way has been provided with a very good permanent flame-retardant finish. The flameproofing test is carried out in accordance with DIN 54,333, "Determination of the speed of flame propagation". After the test flame has been removed, the tufted carpet continues to burn for 50 seconds. After a wet treatment with 2 g/l of a commercially available washing agent for delicate fabrics, for 10 minutes at 40° C., has been carried out three times, the tufted carpet continues to burn for 55 seconds after the test flame has been removed, without reaching the test distance.

Example 13-32:

The tufted carpet described in Example 2, which has a weight per square meter of 650 g and consists of a 6 mm polyamide pile tufted on polypropylene non-woven fabric (about 100 g/m²), is provided with a pre-coat with the aid of a laboratory doctor. The coating must be so regulated that the dry coating is about 780-800 g/m². After the treatment with the doctor, the carpet is dried for 12-15 minutes at 145° C. The pre-coat impregnating solution is of similar composition to that described in Example 2: x parts of the phosphorus-organic compound (Table), x/2 parts of an 80% strength solution of trimethylolmelamine trimethyl ether, 150 parts of a 50% strength butadiene/styrene dispersion (60:40), 400 parts of a 3.5% strength solution of methyl-hydroxyethylcellulose, y parts of water (total batch about 1,495 parts) and 5 parts of chalk. (All parts are parts by weight).

| Example No. | Parts by weight | Moles of P-organic compounds | DIN 54,332 (60") | DIN 54,333 |
|---|---|---|---|---|
| 5b | 250 | 1 pentaerythritol + 4 diethyl meta-1,2-ethanephosphonate + 5.72 EO | continues to burn for 15" | continues to burn for 35" (outside the test distance) |
| 3b | 265 | 1 1,6-hexanediol + (1.33 tetraethyl methane-diphosphonate + 1.33 P₂O₅ + 4.58 EO | continues to burn for 45" | continues to burn for 3' |
| 4f | 210 | 1 1,6-hexanediol + 5 ethane-bis-methylphosphonic acid) anhydride + 6 PyO | does not continue to burn | continues to burn for 60" |
| 9 | 240 | 1 pentaerythritol + (1.33 P₂O₅ + 2.66 tetraethyl methylenediphosphonate) + | continues to burn for 35" | continues to burn for 1'20" |

-continued

| Example No. | Parts by weight | Moles of P-organic compounds | DIN 54,332 (60") | DIN 54,333 |
|---|---|---|---|---|
| 6b | 270 | 1,6-hexanediol + (2.4 moles of diethyl ethanephosphonate + 2 moles of P₂O₅) + 7.2 EO 5.49 EO | does not contine to burn | continues to burn for 2' |
| 6k | 250 | 1 pentaerythritol + (5.44 dimethyl propanephosphonate + 5.08 P₂O₅) + 18.3 EO | does not continue to burn | continues to burn for 2' |
| 6l | 300 | 1 triethanolamine + (2 dimethyl propanephosphonate + 2 P₂O₅) + 7.04 EO | continues to burn for 20" | continues to burn for 30" |
| 6n | 360 | 1 CH₂=C(CH₃)—CO—O—C₂H₄OH + (0.66 dimethyl propanephosphonate + 0.66 P₂O₅) + 3.18 EO | does not continue to burn | burns for 3', 2 cm into the test distance |
| 7 | 240 | 1 hexanediol + (2.0 ethane-bis-(methylphosphonic acid n-butyl ester) + 1.67 P₂O₅) + 8 EO | continues to burn for 10" | continues to burn for 45" |
| 2f | 400 | (HO—C₂H₄—O—(C₆H₂Br₂)—)₂—C(CH₃)₂ + (2 dimethyl propanephosphonate + 2 P₂O₅) + 6.6 EO | does not contine to burn | continues to burn for 20" |
| 8f | 250 | 1 pentaerythritol + (5.35 P₂O₅ + 10.7 triethyl phosphate) + 14.9 EO | — | continues to burn for 1' |
| 6s | 300 | [5.4 C₂H₅—P(O)(OCH₂—CHBr—CH₂Br)₂ + 4.5 P₂O₅] + 1 glycerol + 17.2 EO | does not continue to burn | continues to burn for 40" |
| 10a | 250 | [1 propanephosphonic acid + 5 propanephosphonic acid anhydride] + 7.1 EO | continues to burn for 1'40" | continues to burn for 50" |
| 10b | 280 | 1 glycerol + 9 propanephosphonic acid anhydride + 11.2 EO | does not continue to burn | continues to burn for 10" |
| 11 | 330 | (11.2 ethane-bis-(methyl-phosphinic acid) + 10 propanephosphonic acid anhydride) + 15 ethylene carbonate | does not continue to burn | continues to burn for 10" |
| 12 | 260 | 1 [(HO—P(O)(C₃H₇)—)₂O + 10 1,10-decane-bis-methylphosphinic acid anhydride] + 15.7 EO | continues to burn for 1'10" | continues to burn for 1' |
| 14 | 250 | [(HO)₂P(O)—C₄H₈—P(OH)—)₂O + 18 ethanephosphonic acid anhydride] + 27.2 EO | continues to burn for 1'10" | continues to burn for 35" |
| 17 | 270 | 1 H₃PO₄ + (2 P₂O₅ + 2.07 diethyl propanephosphonate) + 10.3 EO | does not continue to burn | continues to burn for 2' |
| 19c | 280 | H₃PO₄ + (1.33 P₂O₅ + 1.46 triethyl phosphate) + 2 phospholane + 9.8 EO | — | continues to burn for 50" |
| 18 | 260 | propanephosphonic acid + (1.67 P₂O₅ + 1.72 trimethyl phosphate) + 8.4 EO | — | continues to burn for 1' |

"Continues to burn" signifies that, in the case of DIN 54,333, the flames do not reach the 1st mark on the test distance. (Very good values!)

For DIN 54,332, "continues to burn" signifies: after the test flame has been removed the test piece continues to burn for, for example, 10", 1' and the like and is then extinguished.

We claim:

1. Oligomeric phosphorus compounds obtained by (a) reacting at a temperature of 0° to 180° C. 1 mol of a n-hydric alcohol of the formula II $$Z_n\text{—}(OH)_n \quad (II)$$

with about n+e anhydride equivalents of organic phosphorus anhydrides of the formula III $$[R^{AB1}\text{(}O\text{)}_{\overline{f1}}\text{—}A^B\text{—}]_h[\text{—}O\text{—}K\text{—}]_{cK} \quad (III)$$

-continued $$[(\text{—}O\text{—}A^B\text{—})_{\overline{cA}}(O)_{\overline{f2}}\text{—}R^{AB2}]_h$$

in which formulae II and III, $Z_n$ is a functional radical from the group of straight-chain or branched hydrocarbon radicals with 1 to 18 C atoms, which can be interrupted by up to eight —O— and in general by up to (y/2-1) —O—, when y is the number of C atoms in $Z_n$, or by up to two carboxylate groups (—O—CO—) and by up to three —S— and/or $NR^2$ radicals in which $R^2$=(C₁-C₄)-alkyl and/or can be substituted by fluorine, chlorine or bromine; or $Z_n$ is an aromatic or araliphatic radical which is derived from benzene or alkylenebenzenes with up to 18 C atoms or from naphthalene, diphenyl, diphenylmethane, diphenylethane or 2,2-diphenylpropane and which can be substituted in the nucleus by 1 or 2 methoxy or ethoxy groups and can be substituted in the nucleus and/or the side chains by F, Cl oder Br atoms; or $Z_n$ is a phosphorus-containing radical of the formula

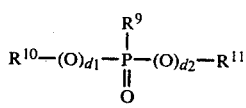

in which $d_1$ and $d_2$ independently of one another are 0 or 1 and $R^9$ is alkyl, hydroxyalkyl, aminoalkyl, mono-$(C_1-C_2)$-alkyl- or dialkyl-aminoalkyl, halogeno-alkyl with 1 to 3 C atoms, alkenyl with 2 or 3 C atoms or phenyl, which can be substituted by 1 or 2 halogen atoms, and $R^{10}$ and $R^{11}$ have the same meaning as $R^9$ when $d_1$ or $d_2$ is 0, or $R^{10}$ and $R^{11}$ are a $(C_1-C_3)$-alkylene radical when $d_1$ and $d_2$ are simultaneously 0, and are a straight-chain or branched alkylene radical with 2-5 C atoms or the radical

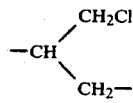

when $d_1$ and $d_2$ are 1, or a phosphorus-containing radical of the general formula

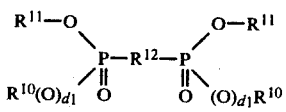

wherein $d_1$, $R^{10}$ and $R^{11}$ are as defined above, $R^{12}$ is alkylene, cycloalkylene, arylene or aralkylene or a group of the formula

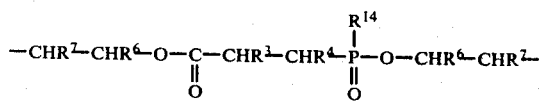

$R^3$ is $(C_1-C_4)$-alkyl which can be substituted by halogen, or is cycloalkyl with up to 8 C atoms, alkylene with up to 4 C atoms, phenyl or benzyl, which can be substituted by halogen, $R^4$ is hydrogen or $(C_1-C_4)$-alkyl, $R^6$ is hydrogen, methyl or chloromethyl, $R^7$ is hydrogen, methyl or ethyl, $R^{14}$ has the meanings defined for $R^3$ or is the group $-O-CHR^6-CHR^7-$, n is 1 to 6, e is number of free acid radicals in the organic phosphorus anhydride and is 0 to 6, $R^{AB1}$ is alkyl or alkenyl each with 1-5 carbon atoms which if $r_1$ is 0, can be substituted by one or two chlorine or bromine atoms or $R^{AB1}$ is hydrogen if $r_1$ is 1, $R^{AB2}$ is alkyl or alkenyl each with 1-5 carbon atoms which, if $r_2$ is 0, can be substituted by one or two chlorine or bromine atoms or $R^{AB2}$ is hydrogen, if $r_2$ is 1 or is $CN-C_2-H_4-$ if $r_2$ is 0, $A^B$ is a group of the formula

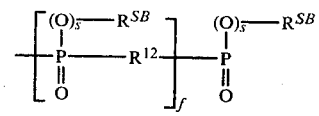

$R^{SB}$ is alkyl or alkenyl each with 1-5 carbon atoms which, if s is 0, can be substituted by one or two chlorine or bromine atoms or $R^{SB}$ is hydrogen if s is 1, f and s are 0 or 1, K is 1 to $C^K$ times a group of the formula

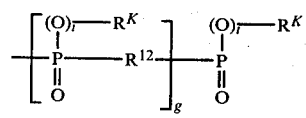

or 0 to $c^K-1$ times a group of the formula

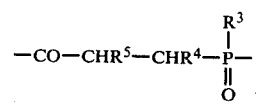

$R^K$ is alkyl or alkenyl each with 1-5 carbon atoms or, if i is zero, $R^K$ is also $(C_1-C_5)$-chloro- or bromoalkyl or cyanoethyl, $R^5$ is hydrogen, methyl or ethyl, i and g are 0 or 1, $c^K$ is 2 to 1200, $c^A$ is 0 or 1, $r_1$ and $r_2$ are 0 or 1 and h is 0 or 1, (b) after the reaction has ended, which is discernible by the disappearance of the anhydride band, mixing the resulting acid reaction product with the at least n+e fold molar amount of an oxalkylating agent of the formula IV

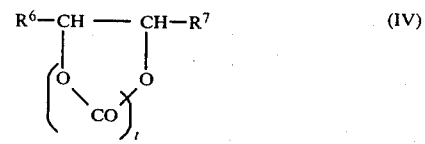

in which t is 0 or 1, converting the mixture, at temperatures of 20° C. to 240° C., when t=0 and at temperatures of 80° to 240° C., when t=1, to the corresponding neutral hydroxyalkyl ester mixture and, after the reaction has ended, which is discernible by the disappearance of the acid number and, when t=1, also of the evolution of $CO_2$, repeating the reaction steps (a) and (b) a total of 0 to 1200 times.

2. Oligomeric phosphorus compounds as claimed in claim 1 which are obtained by mixing an alcohol of the formula III with a total of (n+e)·(1 to 1200) anhydride equivalents of organic phosphorus anhydrides of the formula III and optionally an oxalkylating agent (IV) of low volatility at temperatures of 80° C. to 180° C. and, after the heat of reaction has subsided, reacting the mixture with the at least (n+e)·(1 to 1200) fold molar amount of an oxalkylating agent of the formula (IV) at the particular oxalkylation temperatures, until the reaction has ended - which is discernible by the disappearance of the anhydride bands and, when t=1, also of the evolution of $CO_2$ and of the acid number.

3. Oligomeric phosphorus compounds as claimed in claim 1 which are obtained by reacting at least e·(1 to 1200) anhydride equivalents of the phosphorus anhydrides of the formula III with at least e·(1 to 1200) moles of an or alkylating agent of formula IV until neutral 2-hydroxyalkyl esters are formed.

* * * * *